(12) United States Patent
Markey et al.

(10) Patent No.: US 8,615,303 B2
(45) Date of Patent: Dec. 24, 2013

(54) POWER TRANSFER TO A MEDICAL IMPLANT LOCATED ADJACENT TO TISSUE WHILE PREVENTING SHORT CIRCUITS THROUGH THE TISSUE

(75) Inventors: Mathew Ross Markey, Oatley (AU); Andrew Saldanha, St. Ives (AU)

(73) Assignee: Cochlear Limited, Macquarie University, NSW (AU)

( * ) Notice: Subject to any disclaimer, the term of this patent is extended or adjusted under 35 U.S.C. 154(b) by 112 days.

(21) Appl. No.: 13/030,044

(22) Filed: Feb. 17, 2011

(65) Prior Publication Data

US 2012/0215309 A1 Aug. 23, 2012

(51) Int. Cl.
*A61N 1/00* (2006.01)

(52) U.S. Cl.
USPC .............................. 607/57; 607/61

(58) Field of Classification Search
None
See application file for complete search history.

(56) References Cited

U.S. PATENT DOCUMENTS

| | | | |
|---|---|---|---|
| 5,649,965 A * | 7/1997 | Pons et al. | 607/2 |
| 2006/0271110 A1* | 11/2006 | Vernon et al. | 607/2 |
| 2009/0228077 A1* | 9/2009 | Ginggen et al. | 607/61 |
| 2010/0312310 A1* | 12/2010 | Meskens | 607/61 |

* cited by examiner

*Primary Examiner* — Brian T Gedeon
*Assistant Examiner* — Ankit Tejani
(74) *Attorney, Agent, or Firm* — Kilpatrick, Townsend & Stockton, LLP.

(57) ABSTRACT

A medical implant, including a first power storage device, a first switching circuit for receiving power and transferring the received power from an implant connector electrically connected to the medical implant to the first power storage device in a first power transfer stage, a second power storage device, and a second switching circuit for transferring power from the first power storage device to the second power storage device in a second power transfer stage.

15 Claims, 16 Drawing Sheets

☒ first power transfer stage
☐ second power transfer stage

☒ first power transfer stage
☐ second power transfer stage $V_{P2}$  0V

Iφ1

Iφ2

Iφ3

$V_{P1}$ $V_{P2}$

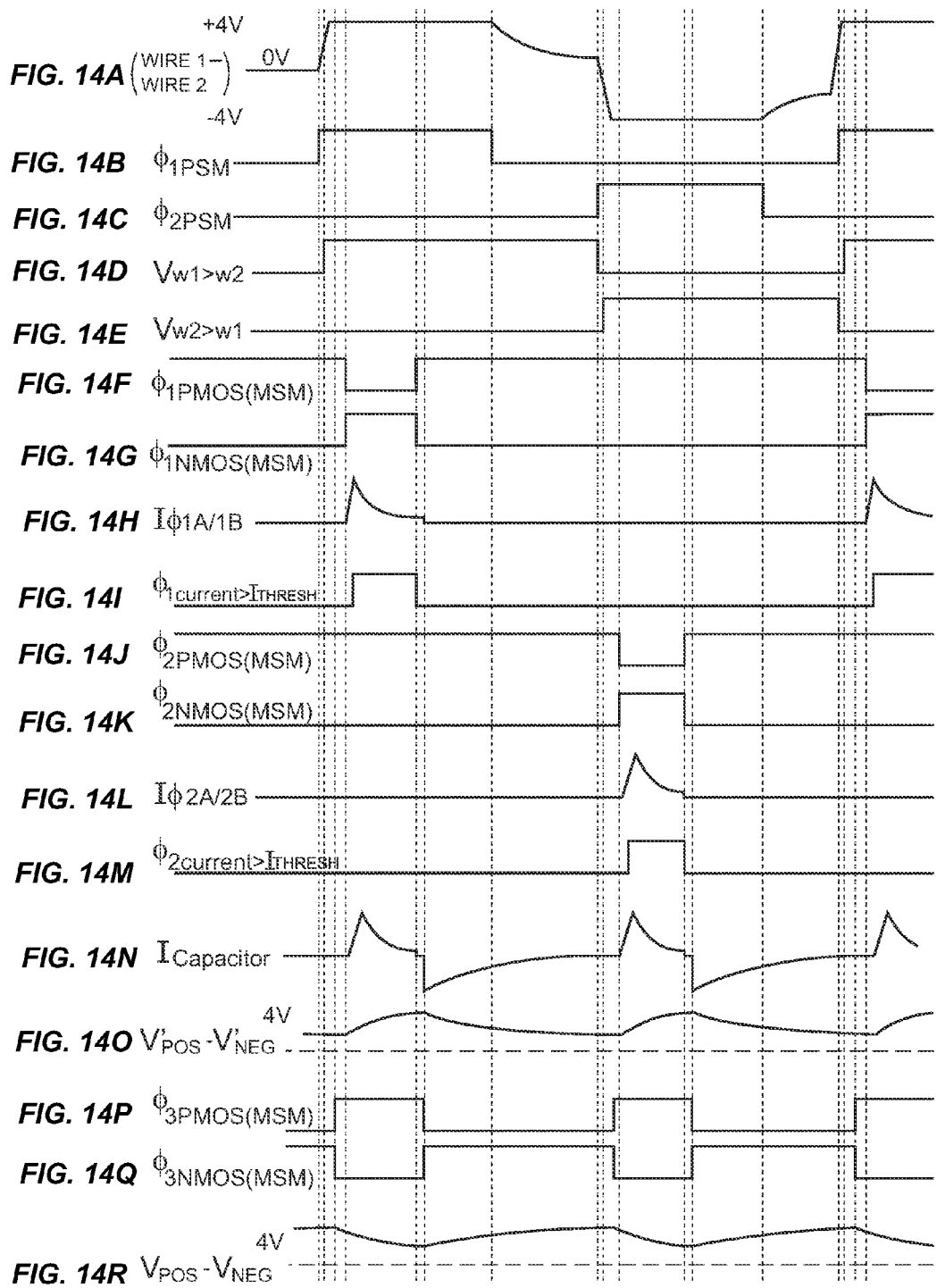

POWER TRANSFER TO A MEDICAL IMPLANT LOCATED ADJACENT TO TISSUE WHILE PREVENTING SHORT CIRCUITS THROUGH THE TISSUE

BACKGROUND

1. Field of the Invention

The present disclosure relates generally to medical implants, and more particularly, to transferring power from one part of the implant to another part of the implant.

2. Related Art

Medical implants require some form of power to operate and perform their intended functions. Sometimes this power is provided from an external power source (i.e., located outside the recipient of the medical implant). Alternatively or in combination with an external power source, the power is provided by an internal power source such as, for example, an implanted battery.

In some medical implants, it is necessary to transfer power to different parts of the implant and/or to different modules of the implant. In medical implants, power storage and power used to drive operational circuits is usually in direct current (DC) form. When transfer or transmission of electrical power is performed within the body of a recipient of the medical implant, there is often utility in avoiding or at least minimizing any contact with tissue of the recipient.

In a medical implant, the DC power source is often converted to alternating current (AC) for transfer across any region that might potentially be exposed to tissue, and then back into DC power for use in powering the medical device or parts thereof.

Damage to a part of the implant (for example the connection path between the two or more parts of the implant), can expose electrically conductive elements to tissue. While the effects of damage to tissue from exposure to the electrical current can be minimised by the use of DC blocking capacitors on the connection paths, the exposed elements can still create a current path through tissue for AC current.

One particular medical device in which such power transfer can be used is a cochlear implant device. A cochlear implant allows for electrical stimulating signals to be applied directly to the auditory nerve fibres of the patient, allowing the brain to perceive a hearing sensation approximating the natural hearing sensation. These stimulating signals are applied by an array of electrodes implanted into the recipient's cochlea.

SUMMARY

According to one aspect of the present invention, there is a medical implant comprising a first power storage device, a first switching circuit for receiving power and transferring the received power from an implant connector electrically connected to the medical implant to the first power storage device in a first power transfer stage, a second power storage device, and a second switching circuit for transferring power from the first power storage device to the second power storage device in a second power transfer stage.

According to another aspect of the present invention, there is a medical implant system comprising a first medical implant, a second medical implant, and an electrical connection between the first and second medical implants, wherein the first medical implant comprises a first power storage device, a power storage interface configured to place the first power storage device into electrical communication with the electrical connection, wherein the second medical implant comprises, a second power storage device, a first switching circuit configured to receive and transfer power received from the electrical connection to the second power storage device in a first power transfer stage, a third power storage device, and a second switching circuit configured to receive and transfer power from the second power storage device to the third power storage device in a second power transfer stage.

According to another aspect of the present invention, there is a method of transferring power between a first medical implant and a second medical implant connected by an electrical connection, the method comprising receiving power from the first medical implant via the electrical connection at the second medical implant, transferring at least a portion of the received power to a first power storage device of the second medical implant via a first switching circuit during a first power transfer stage and storing the received power in the first power storage device, and transferring at least a portion of the stored power stored on the first power storage device to a second power storage device of the second medical implant via a second switching circuit during a second power transfer stage.

BRIEF DESCRIPTION OF THE DRAWINGS

Embodiments of the present invention are described below with reference to the attached drawings, in which:

FIG. 14A shows a waveform of a signal on the two wires in the arrangement of FIG. 13A;

FIG. 14B shows a waveform of the Φ1 clocking signal in the PSM of FIG. 13A;

FIG. 14C shows a waveform of the Φ2 clocking signal in the PSM of FIG. 13A;

FIG. 14D shows the output of the comparator 18 in FIG. 13A;

FIG. 14E shows the output of the comparator 20 in FIG. 13A;

FIG. 14F shows the gate control voltage driving switch 5 in the MSM in FIG. 13A;

FIG. 14G shows the gate control voltage driving switch 6 in the MSM in FIG. 13A;

FIG. 14H shows an approximation waveform of the current flowing in the Φ1 switches in the MSM;

FIG. 14I shows the output of the comparator 13 in the MSM in FIG. 13A;

FIG. 14J shows the gate control voltage that drives the Φ2 PMOS switch 7 in the MSM in FIG. 13A;

FIG. 14K shows the gate control voltage that drives the Φ2 NMOS switch 8 in the MSM in FIG. 13A;

FIG. 14L shows an approximation of the current flowing in the Φ2 switches in the MSM in FIG. 13A;

FIG. 14M shows the output of the comparator 15 in the MSM in FIG. 13A;

FIG. 14N shows the current in the storage capacitor 9' of the MSM in FIG. 13A;

FIG. 14O shows the voltage across the storage capacitor 9' of the MSM in FIG. 13A;

FIG. 14P shows the gate control voltage that drives the Φ3 PMOS switch 21 in the MSM in FIG. 13A;

FIG. 14Q shows the gate control voltage that drives the Φ3 NMOS switch 22 in the MSM in FIG. 13A;

FIG. 14R shows the voltage across the storage capacitor 9 of the MSM in FIG. 13A;

DETAILED DESCRIPTION

An embodiment of the present invention includes a medical implant comprising two separate capacitors located in respective switching circuits. The medical implant receives power from a separate implanted component via an implant connector. The switching circuits are controlled so that a first of the capacitors is in electrical communication with the implant connector so that the first capacitor can be charged with power from the electrical connector during a first power transfer stage. During this first power transfer stage, a second of the capacitors is taken out of electrical communication with the first capacitor. This second capacitor is used to power an electrode of the medical implant to stimulate tissue of a recipient of the medical implant. The switching circuits are further controlled so that the first and second capacitors are in electrical communication with each other so that the second capacitor can be charged with power from the first capacitor during a second power transfer stage. During this second power transfer stage, neither the first capacitor nor the second capacitor is in electrical communication with the electrical connector. This ensures that in the event of a failure of the electrical connector that exposes tissue of the recipient to electricity from the electrical connector, an electrical circuit from the electrical connector, through the electrode, to the circuit containing the second capacitor is never closed, thereby limiting interference with the operation of the electrode.

Figure 1:
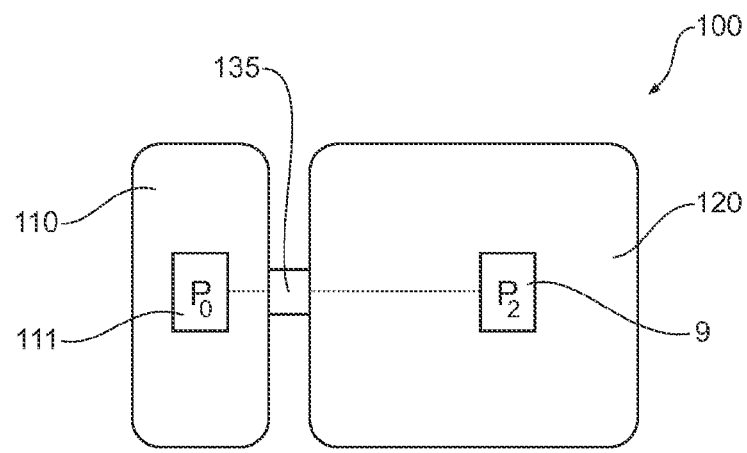
FIG. 1 shows a medical implant with a first module and a second module.

FIG. 1 shows a medical implant system 100 comprising a first module 110 and a second module 120. The two modules are connected together by an implant connector 135. Implant connector 135 can be of any suitable construction and can provide any form of suitable connection. In one form, the connection is a wire connection and could have 1, 2, 3, 4 or more wires connecting first module 110 to second module 120. Further modules can also be connected via implant connector 135 as will be described further below.

First module 110 has a power source $P_0$ 111 which is used to provide power for components within first module 110 as well as to provide power to the second module 120 and/or any further modules connected to first module 110. The power is transferred from the power source 111 of first module 110 to the other modules via a signal transmitted over the implant connector 135. In some embodiments, the power transfer can be bi-directional, that is, power can be transferred from the second module 120 (and/or further modules) to the power source 111 of first module 110.

Second module 120 has its own power storage device $P_2$ 9, which can be used to power circuits and/or other loads associated with second module 120. Power can be transferred to power storage device 9 from the power source in the first module 110 via implant connector 135.

In one aspect, second module 120 provides for a medical implant which has a first power storage device P1 9' and a second power storage device P2 9. Also provided are a first switching circuit 121 for receiving and transferring power from the implant connector 135 to the first power storage device 9' during a first power transfer stage, and a second switching circuit 123 for transferring power from the first power storage device 9' to the second power storage device 9, during a second power transfer stage, as will be described in more detail below.

As previously discussed, transferring power from one module to another module, within a tissue environment, may result in leakage of the signal carrying the power into tissue of the recipient due to, for example, damage to the implant connector or wire insulation. Accordingly, it is generally the case (although not required), that the direct current (DC) power from the power source 111 in the first module 110 is converted into an alternating current (AC) signal prior to transmission over the implant connector 135. The power is then converted back into DC power at the second module 120, for storage in the second power storage device 9 in the second module.

Figure 3A:
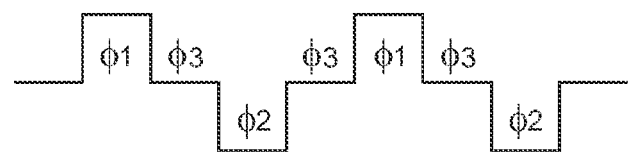
FIG. 3A shows one example of a signal waveform for transmission on the connector.

FIG. 3A shows one example of a signal waveform as driven by the switches in one of the modules (e.g. 110) that could be used in the present arrangement. The waveform is an AC signal having a first phase Φ1 having a first polarity (e.g. positive), a second phase Φ2, having a second, opposite polarity (e.g. negative), and a third phase Φ3, in this case, being undriven (e.g. zero or close to zero voltage). In FIG. 3, the sequence of phases is shown to be Φ1 Φ3 Φ2 Φ3 Φ103 Φ2 . . . i.e. with each of the opposite phases Φ1 and Φ2 being interspersed by the third phase Φ3. It will be seen that the DC balance is zero, providing a utilitarian transmission arrangement, as would be understood.

Figure 3B:
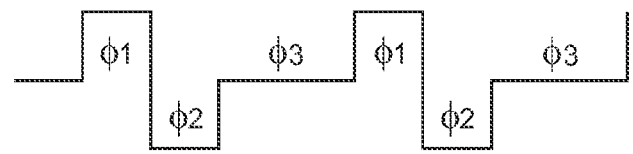
FIG. 3B shows another example of a signal waveform for transmission on the connector.

FIG. 3B shows the signal with the sequence Φ1 Φ2 Φ3 Φ1 Φ2 Φ3 Φ . . . i.e. with phase Φ2 immediately following phase Φ1 and then followed by the third phase Φ3. Again, the DC balance is zero.

Figure 2:
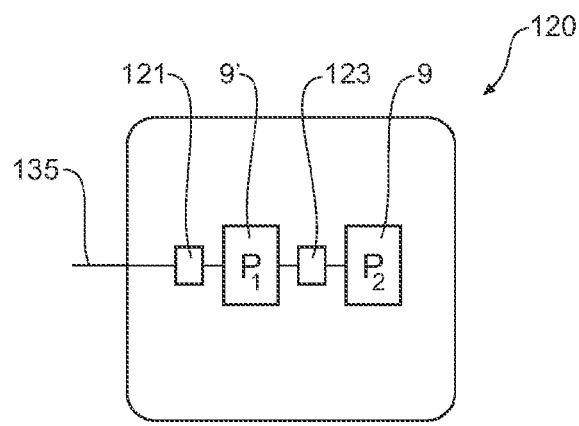
FIG. 2 shows a medical implant corresponding to the second module of FIG. 1.
Figure 4:
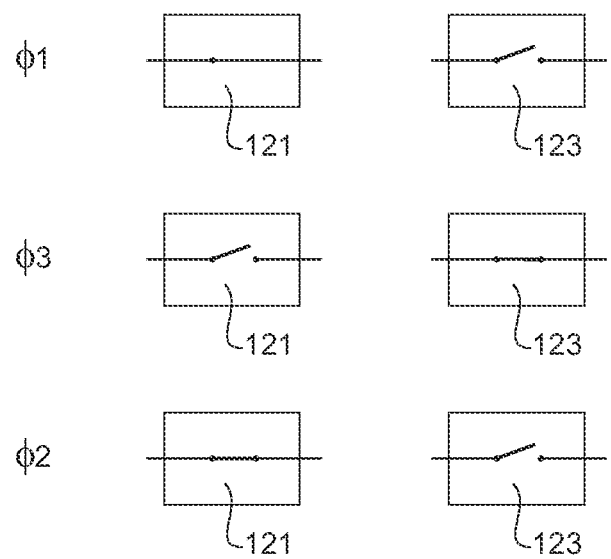
FIG. 4 schematically depicts the operation of the first and second switching circuits of FIG. 2 as the signals of FIGS. 3A and 3B change.

FIG. 4 shows the operation of the first switching circuit 121 and the second switching circuit 123 of FIG. 2 with respect to the phases of the signal in FIGS. 3A and 3B. During phase Φ1, first switching circuit 121 is closed (i.e., the first switching circuit 121 is conducting), to allow power to be transferred from the implant connector 135 to the first power storage device 9'. During phase Φ1, the second switching circuit 123 is open (i.e., the second switching circuit 123 is non-conducting), thereby electrically isolating the first power storage device 9' from the second power storage device 9, for reasons that will be described in more detail below.

FIG. 4 also shows that in the next phase, which when the signal transferred over implant connector 135 is as shown in FIG. 3A, is the third phase Φ3, first switching circuit 121 is open (i.e., the first switching circuit 121 is non-conducting), thereby isolating first power storage device 9' from the implant connector 135 and thus the outside of the medical implant itself. During this third phase, second switching circuit 123 is closed (i.e., the second switching circuit 123 is conducting), thereby electrically connecting second power storage device 9 to the first power storage device 9'. This allows the stored power in first power storage device 9' to be transferred to the second power storage device 9, for use in powering the circuitry or loads of second module 120.

In the next phase, as shown in FIG. 4, which is phase Φ2, the second switching circuit 123 is open, (non-conductive), thereby electrically isolating the second power storage device 9 from the first power storage device 9', while the first switching circuit 121 is closed (conductive), thereby connecting first power storage device 9' to the implant connector, and thus the power source 111, to allow further transfer of power from the power source 111 in the first module 110 to the second module 120.

Thus, this arrangement provides for two power transfer stages. During the first power transfer stage, power is transferred from the implant connector or an entry port of the second module, to the first power storage device 9'. During the second power transfer stage, power is then transferred from the first power storage device 9' to the second power storage device 9.

Figure 5A:
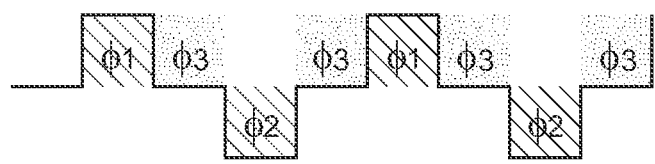
FIG. 5A shows the first and second power transfer stages over the signal of FIG. 3A.
Figure 5B:
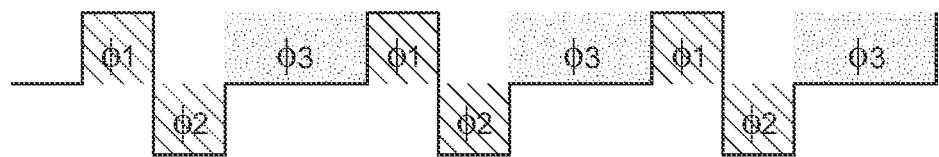
FIG. 5B shows the first and second power transfer stages over the signal of FIG. 3B.

FIGS. 5A and 5B illustrate how the first and second power transfer stages can be mapped onto the signals shown in FIGS. 3A and 3B. In the signal pattern of FIG. 5A, corresponding to the signal pattern of FIG. 3A, the first power transfer stage is shown as a lined area encompassing first and second phases Φ1 and Φ2, with the second power transfer stage, shown as a dotted area, encompassing third phase Φ3.

With respect to the signal of FIG. 5B, corresponding to the signal of FIG. 3B, it can be seen that the first power transfer stage encompasses both the first and second phases Φ1 and Φ2 together, followed by the second power transfer stage, encompassing the third phase Φ3.

FIGS. 6A to 6E show various waveforms in the arrangement of FIG. 2, as the signal on implant connector 135 varies over the various phases.

Figure 6A:
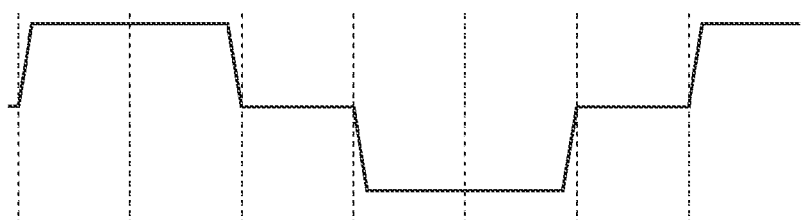
FIG. 6A shows the waveform of the signal on the connector of FIG. 2.
Figure 6B:
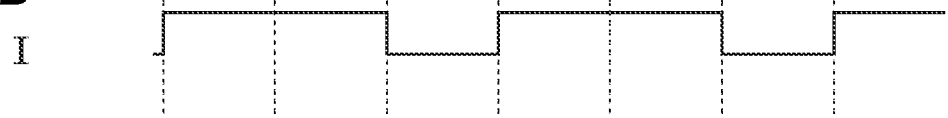
FIG. 6B shows the current through the first switching circuit of FIG. 2.
Figure 6C:
FIG. 6C shows the current through the second switching circuit of FIG. 2.

FIG. 6A shows the signal on implant connector 135 as it varies over first, second and third phases. This waveform corresponds to that of FIGS. 3A and 5A, with a more realistic finite rise-time. FIG. 6B shows the current Is121 through first switching circuit 121 as the signal in FIG. 6A varies. As can be seen, when the signal in FIG. 6A is positive (as in phase Φ1), first switching circuit 121 is closed, allowing current to flow through the circuit and to allow power to transfer to the first power storage device 9' in the first power transfer stage. When the signal enters the third phase Φ3, the first switching circuit 121 opens, and current stops flowing through the switch. In this third phase, second switching circuit 123 closes, allowing current Is123 to flow through the second switching circuit to allow power to transfer from the first power storage device 9' to the second power storage device 9, in the second power transfer stage, as shown in FIG. 6C. When the signal becomes negative, in phase Φ2, first switching circuit closes again, allowing current to flow through again, in the first power transfer stage, while the second switching circuit 123 opens, isolating the second power storage device from the first power storage device again.

Figures 6D, 6E:
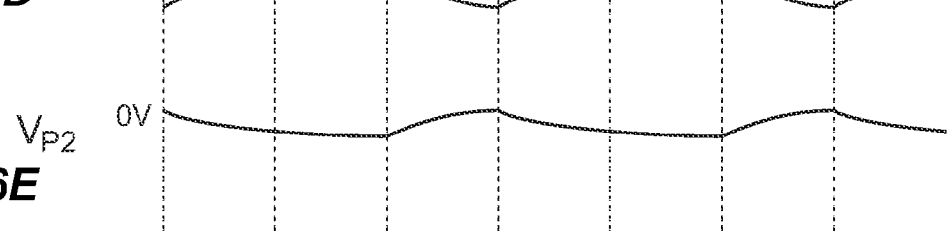
FIG. 6D shows the voltage across the first power storage device of FIG. 2.
FIG. 6E shows the voltage across the second power storage device of FIG. 2.

FIG. 6D shows the voltage VP1 across the first power storage device 9' as the first and second switching circuits open and close. It can be seen that when the first switching circuit 121 is closed, allowing power to transfer from the implant connector 135 to the first power storage device 9', the voltage across the device increases. When the first switching circuit opens, electrically isolating first power storage device 9' from the implant connector and thus the power source 111, the voltage stops increasing, and begins to decrease as the second switching circuit 123 closes and allows the power stored on the first power storage device 9' to be transferred to the second power storage device 9, in the second power transfer stage. As the signal in FIG. 6A enters the second phase Φ2, the first switching circuit 121 closes and the second switching circuit 123 opens, allowing the power transfer to continue to charge up the first power storage device 9' in the first power transfer stage, resulting in the voltage VP1 increasing again.

FIG. 6E shows the voltage VP2 as the signal varies. During the time that the first power storage device 9' is charging up when the signal in FIG. 6A is in the first phase Φ1 and in the first power transfer stage, the voltage on second power storage device 9 begins to reduce, as loads being powered by the second power storage device drain some of the power. As the signal in FIG. 6A enters the third phase Φ3, and the second power transfer phase, the power stored in the first power storage device 9' is now transferred to the second power storage device 9, resulting in an increase in the voltage of VP2. When the signal enters the second phase Φ2 and the first power transfer phase, the voltage stops increasing and begins to discharge again as it did during the first phase, until the next second power transfer phase, when the power is again transferred from the first power storage device 9' to the second power storage device 9.

Figure 7:
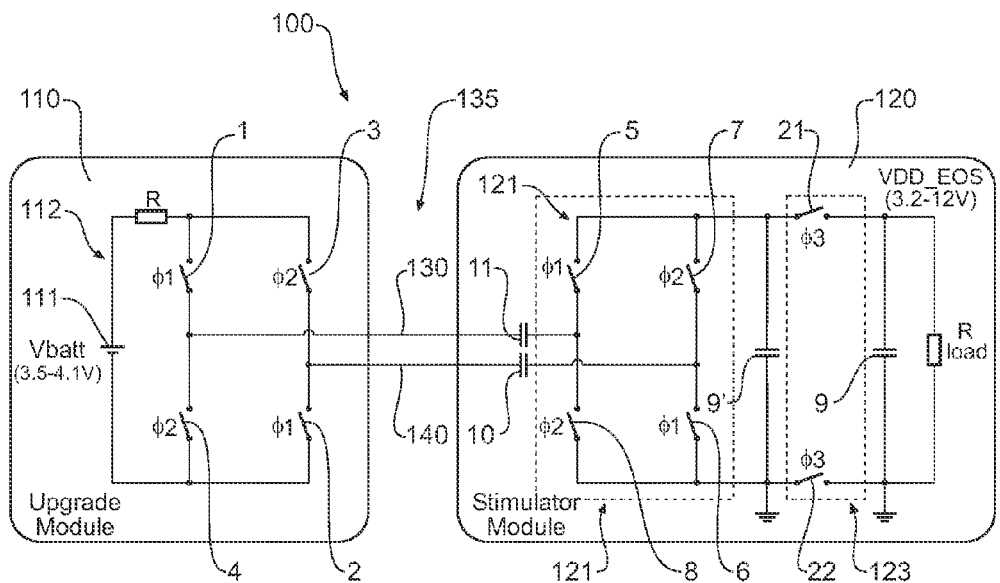
FIG. 7 shows an exemplary circuit diagram of the medical implant of FIG. 1 with two modules.

FIG. 7 shows another embodiment of the general arrangement shown in FIGS. 1 and 2. In this arrangement, medical implant system 100 comprises first module 110 and second module 120, connected by implant connector 135. In this example, implant connector 135 is a two-wire connector, with wires 130 and 140.

First module 110 has power source 111 in the form of a battery, as well as a power source switching circuit 112 comprising switches 1, 2, 3 and 4. These switches coordinate to convert the DC power from battery 111 into the AC signal for transmission over wires 130 and 140. The signal thus generated will have the form as shown in, for example, FIG. 3A or 3B, with the Φ1 switches (1 and 2) closing to generate the Φ1 portion of the signal, the Φ2 switches (3 and 4) closing to generate the Φ2 portion of the signal, and all switches opening to generate the Φ3 portion of the signal. Of course, it will be appreciated that any form of AC signal generator can be used to generate the signal for transmission on wires 130 and 140.

The second module, 120, in this example, has its first switching circuit 121 provided by corresponding four switches 5, 6, 7 and 8, with Φ1 switches (5 and 6) coordinating to pass through the Φ1 portion of the signal to charge first power storage device 9', and Φ2 switches 7 and 8 coordinating to pass through the Φ2 portion of the signal to first power storage device 9'. In this way, the first switching circuit 121 also acts as a rectifier circuit to convert the incoming AC signal to a DC signal for storage in the second module 120.

In this example, second switching circuit 123 is provided by two switches 21 and 22, acting as the Φ3 switches which coordinate to close during the Φ3 phase to transfer the power stored on first power storage device 9' to the second power storage device 9 during the second power transfer stage as previously described. FIG. 7 also shows load R of the second module 120 which can comprise functional elements of the implant such as operational circuitry and/or stimulation circuitry as will be described in more detail below.

In the exemplary embodiment of FIG. 7, there are also DC blocking capacitors 10 and 11 to block any DC components on the two wires 130, 140.

Figure 8:
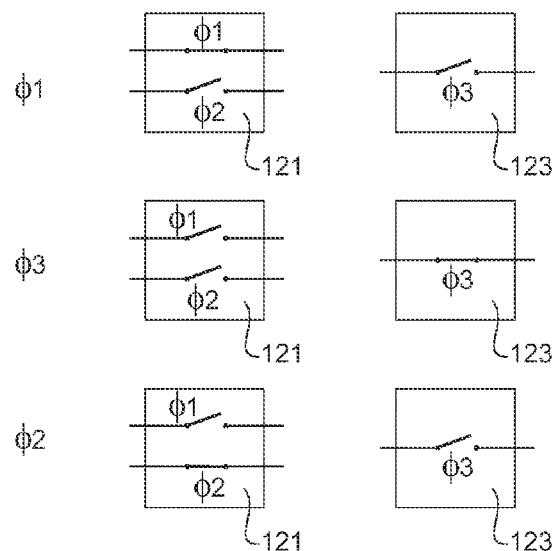
FIG. 8 schematically depicts the operation of the first and second switching circuits of FIG. 7 as the signals of FIGS. 3A and 3B change.

FIG. 8 presents a schematic depicting switch position relative to phase for the embodiment depicted in FIG. 7, with two switches for each phase.

In the first phase Φ1, the Φ1 switches 5 and 6 of first switching circuit 121 are closed to allow the Φ1 portion of the signal to pass through to the first power storage device 9'. In this phase, the Φ2 switches 7 and 8 of the first switching circuit 121 and the Φ3 switches 21 and 22 of the second switching circuit 123 are open, so as to be non-conducting, and in the case of the Φ3 switches, to electrically isolate the second power storage device 9 from the first power storage device 9' and the two wires 130 and 140 of implant connector 135, as well as from the power source 111 of the first module 110.

When the signal enters the third phase Φ3, both the Φ1 and Φ2 switches 5, 6 and 7,8 respectively, of the first switching circuit 121 are open, and the Φ3 switches 21 and 22 of the second switching circuit 123 are closed, electrically connecting the second power storage device 9 to the first power storage device 9', thus allowing the power stored on the first power storage device 9' to be transferred to the second power storage device 9 in the second power transfer stage.

When the signal enters the second phase Φ2, the Φ1 switches 5 and 6 remain open while the Φ2 switches 7 and 8 close to electrically connect the first power storage device 9' to the wires 130, 140 and to allow the Φ2 portion of the signal to charge up the first power storage device 9' in the first power transfer stage. In this Φ2 phase, the Φ3 switches 21 and 22 of the second switching circuit 123 are open to isolate the second power storage device 9 from the first power storage device 9'.

FIGS. 9A to 9F show various waveforms at different points in the arrangement of FIG. 7 as the signal varies across the three phases. These figures accord with FIGS. 6A to 6E, but illustrating the case where there are two switches per phase as in FIG. 7.

Figure 9A:
FIG. 9A shows the waveform of the signal on the connector of FIG. 7.
Figure 9B:
FIG. 9B shows the current through the Φ1 switches of the first switching circuit of FIG. 7.
Figure 9C:
FIG. 9C shows the current through the Φ2 switches of the first switching circuit of FIG. 7.
Figure 9D:
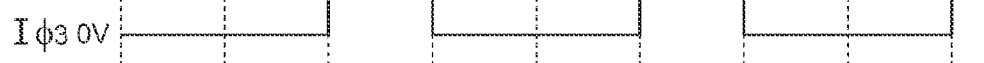
FIG. 9D shows the current through the Φ3 switches of the second switching circuit of FIG. 7.

FIG. 9A shows the signal on implant connector 135, wires 130 and 140 as it varies over first, second and third phases. This waveform corresponds to that of FIGS. 3A and 5A, with a more realistic finite rise-time. FIG. 9B shows the current I Φ1 through the Φ1 switches 5 and 6 of first switching circuit 121 as the signal in FIG. 9A varies. As can be seen, when the signal in FIG. 9A is positive (as in phase Φ1), the Φ1 switches in first switching circuit 121 are closed, allowing current to flow through the circuit and to allow power to transfer to the first power storage device 9' in the first power transfer stage. When the signal enters the third phase Φ3, the Φ1 switches in the first switching circuit 121 open, and current stops flowing through the switches. In this third phase, the Φ3 switches in the second switching circuit 123 close, allowing current I Φ3 to flow through the second switching circuit to allow power to transfer from the first power storage device 9' to the second power storage device 9, in the second power transfer stage, as shown in FIG. 9D. When the signal becomes negative, in phase Φ2, the Φ2 switches 7 and 8 of the first switching circuit close, while the Φ1 and Φ3 switches open, allowing current I Φ2 to flow through first switching circuit 121 (FIG. 9C), in the first power transfer stage, while the second switching circuit 123 opens, isolating the second power storage device from the first power storage device again.

Figure 9E:
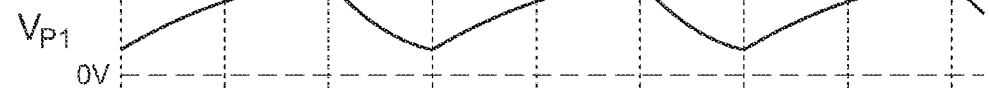
FIG. 9E shows the voltage across the first power storage device of FIG. 7.

FIG. 9E shows the voltage VP1 across the first power storage device 9' as the first and second switching circuits open and close. It can be seen that when the first switching circuit 121 is closed, allowing power to transfer from the implant connector 135 to the first power storage device 9', the voltage across the device increases. When the first switching circuit opens, electrically isolating first power storage device 9' from the implant connector and thus the power source 111, the voltage stops increasing, and begins to decrease as the second switching circuit 123 closes and allows the power stored on the first power storage device 9' to be transferred to the second power storage device 9, in the second power transfer stage. As the signal in FIG. 9A enters the second phase Φ2, the first switching circuit 121 closes and the second switching circuit 123 opens, allowing the power transfer to continue to charge up the first power storage device 9' in the first power transfer stage, resulting in the voltage VP1 increasing again.

Figure 9F:
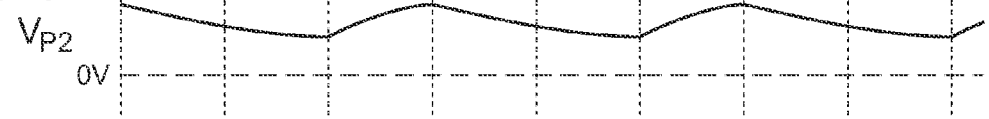
FIG. 9F shows the voltage across the second power storage device of FIG. 7.

FIG. 9F shows the voltage VP2 as the signal varies. When the first power storage device 9' is charging up when the signal in FIG. 9A is in the first phase Φ1 and in the first power transfer stage, the voltage across the second power storage device 9 is discharging due to being drawn on by the load. As the signal in FIG. 9A enters the third phase Φ3, and the second power transfer phase, the power stored in the first power storage device 9' is now transferred to the second power storage device 9, resulting in an increase in the voltage of VP2. When the signal enters the second phase Φ2 and the first power transfer phase, the voltage stops increasing and discharges, until the next second power transfer phase, when the power is again transferred from the first power storage device 9' to the second power storage device 9.

It will also be understood that the reverse operation is possible. In some cases, second power storage device 9 can act as the power source, to provide power for transfer to the power source or battery 111 in the first module or PSM 110. In this procedure, second switching circuit 123 is closed, allowing stored power to transfer from second power storage device 9 to first power storage device 9'. The second switching circuit 123 then opens to isolate second power storage device 9 from first power storage device 9' and first switching circuit closes to electrically connect first power storage device 9' to the battery for example, in first module 110. In this case, first switching circuit 121 is acting as an inverter, converting DC power from the first power storage device 9' to an AC signal for transfer over implant connector 135. At first module 110, the received AC signal can then be rectified to provide power to charge up battery 111.

Figure 10A:
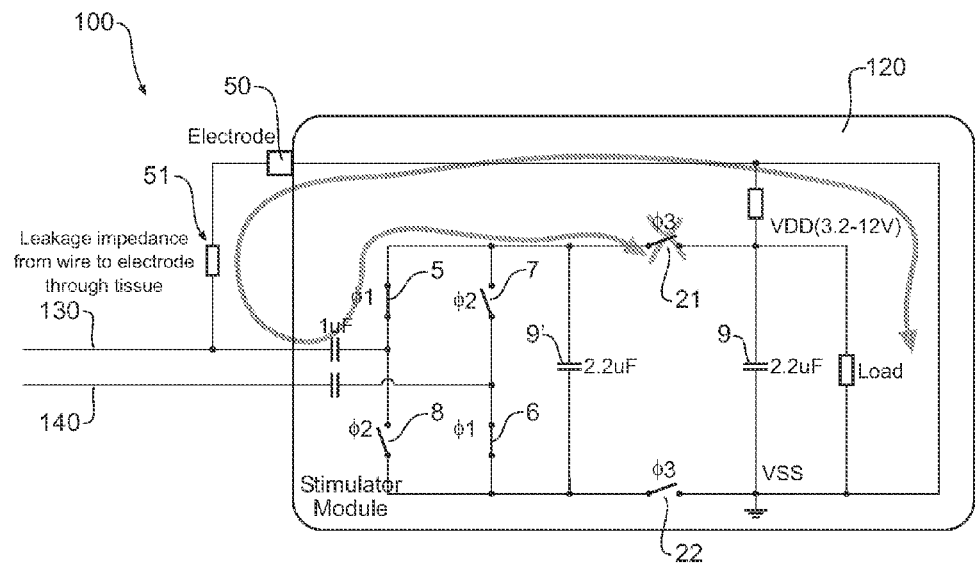
FIG. 10A shows a potential circuit path through tissue in the first power transfer phase of the circuit depicted in FIG. 7.
Figure 10B:
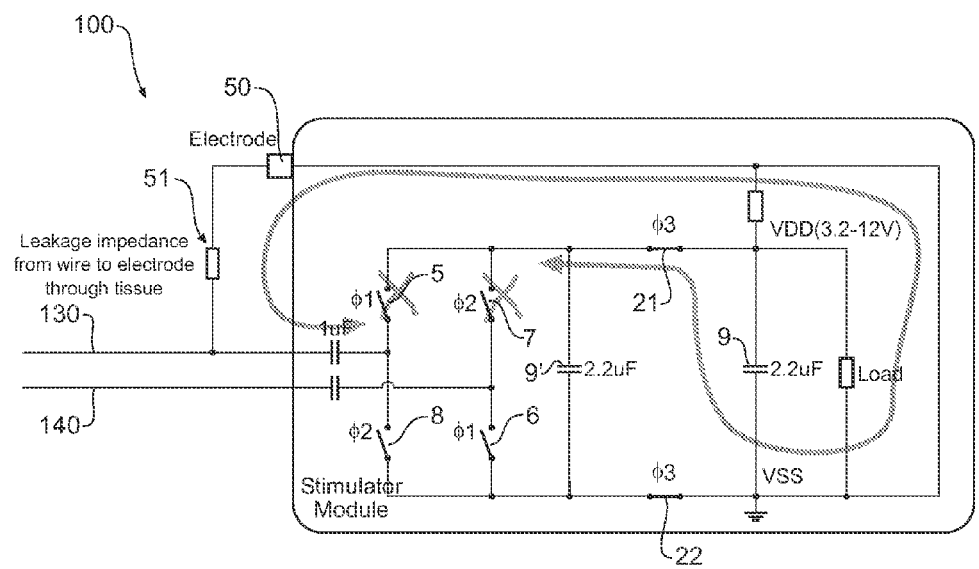
FIG. 10B shows a potential circuit path through tissue in the second power transfer phase in the circuit depicted in FIG. 7.

FIGS. 10A and 10B illustrate how the embodiments described above reduce the risk of current leakage to tissue in the event of a breach in the integrity of a part of the implant 100, such as for example, implant connector 135. FIG. 10A illustrates a medical implant 100, being a second module in this case, of a medical device with a stimulator such as an electrode array of a cochlear implant. FIG. 10A shows implant 120 according to the arrangement of FIG. 7, with wires 130 and 140 delivering a signal including at least a power component, to the implant 120. While the embodiment depicted in FIG. 10A with respect to element 100 is a stimulator of a cochlear implant, in other embodiments, element 100 is a stimulator/receiver of a cochlear implant.

As shown in FIG. 10A, the electrode array 50 is powered indirectly by second power storage device 9, which also powers other functional elements of the implant. If there were to be a breach in the insulation of wire 130 for example, this would electrically expose the conductive wire 130 to the surrounding tissue, creating an electrical path or circuit between the electrode array 50 and the breach, through the surrounding tissue. This path is represented by leakage impedance path 51. Accordingly, when electrode array 50 generates an AC current to stimulate the implantee's hearing cells, as is the function of the cochlear implant, current would normally also be conducted along the leakage path 51, into the implant 120 and back to the common earth or positive terminal of the second power storage device 9. However, as shown in FIG. 10A, because of the arrangement described, and the provision of the first power storage device 9', which acts as an intermediary power storage device, it is possible to isolate the second power storage device 9 which powers the electrode array 50 from the first power storage device 9', which breaks the current circuit path, thereby preventing the leakage path from forming.

Thus it can be seen in FIG. 10A that during the first power transfer stage when the first power storage device 9' is electrically connected to the wires 130 and 140, second power storage device 9, is electrically isolated from this path because the Φ3 switches 21 and 22 are open, thus preventing the completion of a circuit path from the second power storage device 9 through the electrode array 50 and through the leakage path 51, back to the second power storage device 9. This break in the path is illustrated by the drawn line and the cross at the switch 21.

FIG. 10B illustrates the situation in the second power transfer stage (in phase Φ3), when the phase Φ1 and Φ2 switches (in this case the entire first switching circuit) are open and thus non-conducting, and the Φ3 switches are closed. The drawn line illustrates that the current circuit path is broken (at the crosses) during the second power transfer stage while power is being transferred from the first power storage device 9' to the second power storage device 9.

It will be appreciated that even if there is some small overlap in time between the opening and closing of the relevant switches between the first power transfer stage and the second power transfer stage, and the transitions between the switching in the three phases Φ1, Φ2 and Φ3, the risk of damage is still reduced, since there is not a constant closed circuit provided for the leakage current to flow.

In some embodiments however, the operation of the various switches can be coordinated such that there will be substantially no overlap in time when the Φ1, Φ2 and Φ3 switches are closed. Various embodiments of this aspect will now be described below, with specific reference to a cochlear implant and cochlear implant system, although it will be appreciated that the various aspects described can be applied to any other medical implant or implant system.

Figure 11:
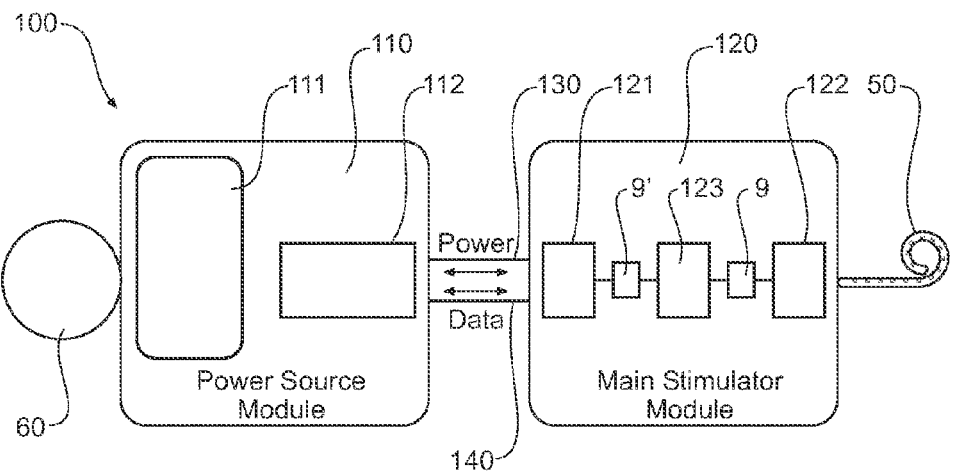
FIG. 11 shows a stimulator and/or a stimulator/receiver of a cochlear implant comprising a first module and a second module.

FIG. 11 shows a medical implant 100 such as a stimulator/receiver 100, being an implantable part of a medical implant system such as a cochlear implant system. Stimulator/receiver 100 is in this example, made up of two modules—a first module, being in this case a power source module (PSM) 110 including a receiver component, and a second module, being in this case, a main stimulator module (MSM) 120 including a stimulator component.

Power source module 110 houses a power source 111 such as a battery, which can be rechargeable and/or removable. If the battery is to be recharged, recharging can be done via coil 60. Coil 60 can also be used for receipt of control signals from the external processor (not shown). Power source module 110 also includes two-wire interface 112 which will be described in more detail below. Two-wire interface 112 interfaces power source 111 with two wires 130 and 140 connecting power source module 110 and main stimulator module 120 as will be described in more detail below. Collectively, wires 130 and 140 make up an electrical connection between the PSM 110 and the MSM 120.

Main stimulator module 120 includes load 122 (such as stimulator control circuitry and electrode array 50) and first switching circuit or two-wire interface circuit 121, which interfaces between the two wires 130 and 140 and the main stimulator module 120. Also provided is first power storage device 9', second switching circuit 123 and second power storage device 9, which provides power for the implant load 122 including stimulating electrode array 50.

Main stimulator module 120 connects to electrode array 50 which in use, is inserted into a recipient's cochlea for normal electrical stimulation as will be understood by the person skilled in the art.

The arrangement shown in FIG. 11 allows for power source module 110 to be removed or otherwise separated from main stimulator module 120. In some embodiments, this provides utility in the event that the power source 111 needs to be replaced or otherwise removed. For example, the surgery required is less serious, invasive or extensive than if the entire stimulator 100 had to be removed (e.g., there is no need to remove the implanted electrode array 50).

Any suitable connector can be used to connect power source module 110 to main stimulator module 120. For example, a connector currently used in pacemaker devices can be used.

In the arrangement shown in FIG. 11, two wires 130 and 140 are used to deliver power from power source module 110 to main stimulator module 120. In some instances, two wires 130 and 140 can also be used to transfer data between the two modules.

It will also be appreciated that the direction of power and data flow can be both from the first module or power source module to the second module or main stimulator module, or from the second module or main stimulator module to the first module or power source module, or indeed a combination of both.

It will also be appreciated that the various aspects described herein need not be applied to a power source module and a main stimulator module of a stimulator, but can indeed be applied to a power source module and another type of module or device such as a sensor device or other implantable medical device that is required to obtain power from the power source module.

As previously described, embodiments of the present invention strive to avoid the exposure of tissue of a recipient to DC current. Accordingly, because there is a risk of exposing the power transferring between the first module and the second module to tissue (for example in the event of damage to insulation), in some embodiments of the present invention, power is transmitted as an alternating current (AC) signal.

Accordingly, the function of the two-wire interface 112 in the power source module is to enable the conversion of the DC power from the power source or battery 111 into an AC signal for transmission on the two wires 130 and 140. In the event that power is being transferred to the power source module 110 from the main stimulator module 120, two-wire interface 112 will act as a rectifying circuit to convert the incoming AC signal to DC to charge the power source 111.

Similarly, the two-wire interface or first switching circuit 121 of the main stimulator module 120, will act to enable the conversion of the input AC power on two wires 130 and 140 into a DC signal for use in powering circuitry in or associated with main stimulator module 120. In the event that power is being transferred from the main stimulator module 120 to power source module 110, two-wire interface or first switching circuit 121 will act to enable conversion of the DC power to AC power for transmission on two wires 130 and 140.

In the following section of the description, the examples given will be in relation to power source module 110 supplying power to main stimulator module 120. It will also be assumed that power source module 110 will act as the master module and the main stimulator module 120 will act as the slave module, although this need not necessarily always be the case. In some cases, main stimulator module 120 can act as the master and power source module 110 can act as the slave module, irrespective of the direction of flow of power. It will be understood that when it is said that the power module is acting as the master, it is meant that the function of some elements (in this particular example, the two-wire interface 112 generating the AC signal) of the power module act independently of external information, while the main stimulator module, acting as the slave module, will function in accordance with information produced by the master module (in this particular example, the two-wire interface 121 of the main stimulator module 120 will act in accordance with the input AC signal generated by the master module)

Figure 12:
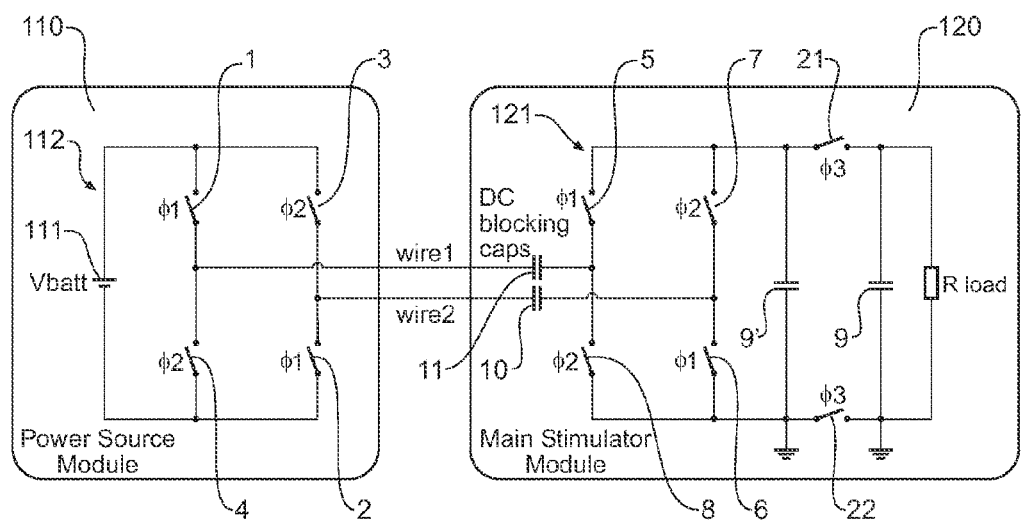
FIG. 12 shows a circuit diagram of the stimulator and/or stimulator receiver of FIG. 11 showing an exemplary switching arrangement for the two-wire interfaces.

Turning now to FIG. 12, there is shown power source module (PSM) 110 and main stimulator module (MSM) 120, having respective two-wire interface 112 and 121 (acting as the first switching circuit). As shown, two-wire interfaces 112 and 121 include an arrangement of switches that can be selectively controlled to perform the inverter and rectification functions referred to above.

With reference to the PSM (assuming that it is the Master in this example), in this embodiment there are 4 switches, 1, 2, 3 and 4. The switches (1 and 2) labelled Φ1 are closed during a first phase of the AC signal (see FIGS. 3A and 3B) and the switches (3 and 4) labelled 12 are open. This results in a positive voltage difference of about Vbatt between wire1 and wire2. Similarly, during a second phase of the AC signal, the Φ2 switches (3 and 4) are closed and the Φ1 switches (1 and 2) are open, producing a negative voltage difference of about Vbatt (voltage of the power source or battery 111) between the wire1 and wire2. This arrangement accordingly performs an inversion of the DC battery voltage into an AC voltage between the wires, without any DC component.

With reference to the MSM (assuming that it is the Slave in this example), four switches 5, 6, 7 and 8 are provided for the first switching circuit 121. The same timing of the Φ1 and Φ2 switches as in the PSM would rectify the AC voltage between the wires onto a first power storage device such as storage capacitor 9' (in this example), with minimal losses compared with a passive diode rectifier.

This arrangement results in current being drawn from the battery in the PSM to charge the storage capacitor or first power storage device 9' in the MSM during both phases.

In one embodiment, use of series capacitors 10 and 11 can be made in the MSM to block any DC current from flowing between either wire and the electrode array connected to the PSM, in the event of a breach of the insulation surrounding the wires. It will however be understood that blocking capacitors 10 and 11 are not necessarily required.

Also shown are the switches 13 switches, switches 21 and 22, forming the second switching circuit, connecting the second power storage device 9 to the first power storage device 9'. In this case, second power storage device 9 can also be a capacitor.

It will be appreciated that if the timing of the switching from phase 1 to phase 2 and vice versa is not correct, there will be a time where the positive terminal of first power storage device 9' can be connected to the negative terminal of the battery 111 or that the negative terminal of first power storage device 9' will be connected to the positive terminal of battery 111. In this situation, capacitor 9' will actually discharge rather than charge, resulting in a reduction in the efficiency of the power transfer from PSM 110 to MSM 120.

According to one aspect hereindescribed therefore, the timing of the switching in the first power storage device 121 is controlled such that at no time is there provided an electrical path from one polarity of the first power storage device 9' or capacitor, to the opposite polarity of the power source or battery 111. This is accomplished in one form by controlling the switches 5, 6, 7 and 8 in the MSM 120, such that a closed (or conducting) switch is caused to be open (non-conducting) prior to a change in polarity of the AC signal. In this way, at no time will there be a return or discharge path to allow the power storage device to discharge into the power source. It will be understood by those skilled in the art that the opening of a switch is not instantaneous, and that a finite amount of time elapses between the beginning of the opening of the switch to the time that the switch is fully open and non-conducting. During this finite time, the switch is still conducting. Accordingly, beginning to open the switch upon reversal of polarity will result in the switch still conducting momentarily during the reversed polarity, resulting in discharge of the power storage device.

In one embodiment, this is avoided by causing the switches 5, 6, 7 and 8 to begin opening (or becoming non-conductive) at some time prior to the AC signal which the switch is conducting, reversing polarity. In one form, this is accomplished by monitoring a current magnitude in the AC signal, and causing the switch to begin opening when this magnitude falls below a predetermined threshold.

In another embodiment, the control of the opening of the switches is caused to occur in accordance with a timing signal rather than with reference to the incoming AC signal.

Each of these embodiments incorporating the various aspects described herein will now be described in more detail with reference to FIGS. 13A, 13B, 13C, 14, 15 and 16.

Figure 13A:
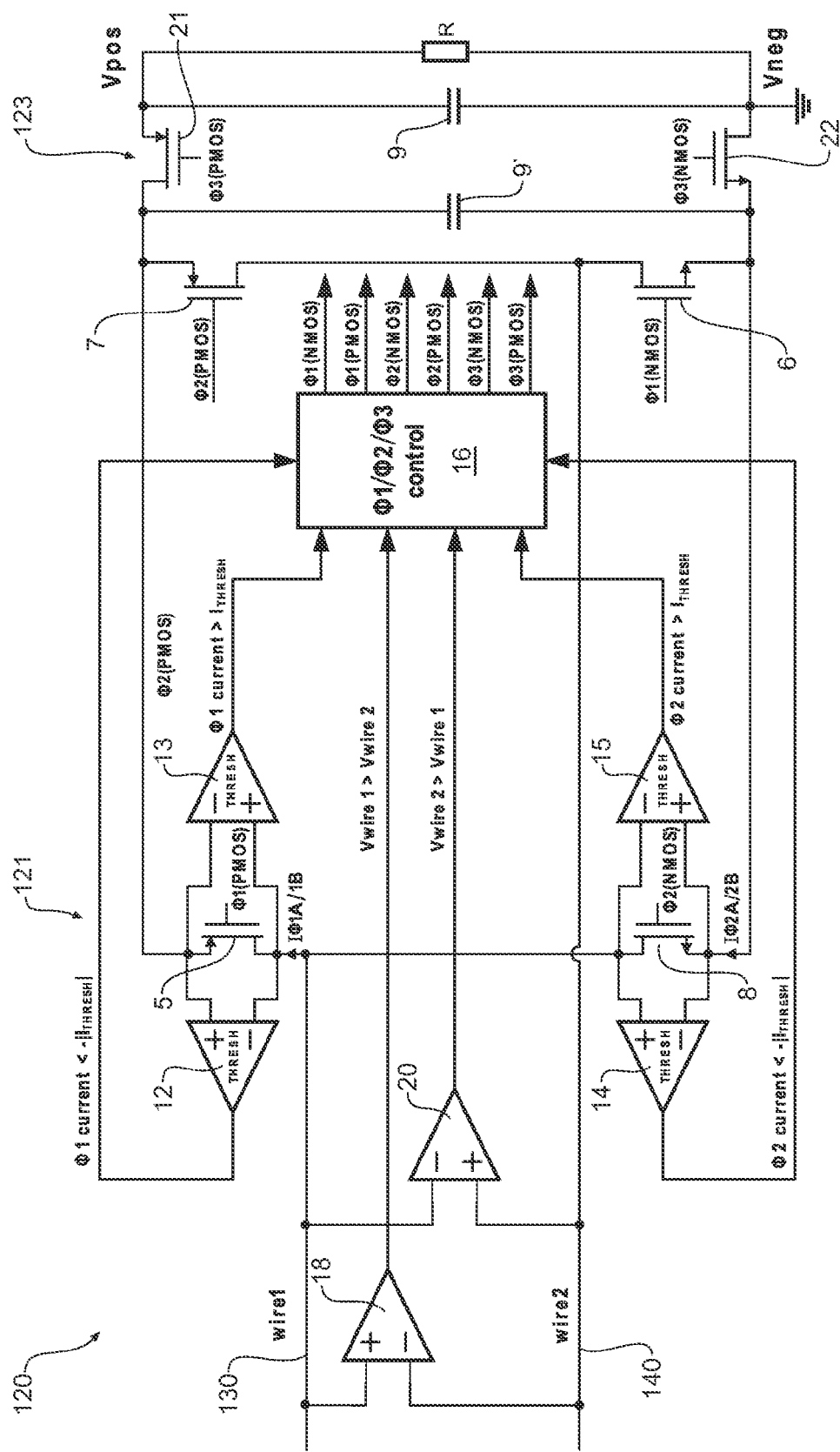
FIG. 13A shows an embodiment of a circuit in which the opening of the switches is controlled according to current level.

In FIG. 13A, there is shown one example of a circuit which can be used in the MSM. The first switching circuit 121 includes the four switches 5, 6, 7 and 8 described above with reference to FIG. 12. Low-current detectors 12, 13, 14 and 15 detect when the current through the switches drops below the threshold, switch control block 16, and voltage comparators 18 and 20 for detecting the change in voltage or polarity of the signal on lines 130 and 140. In this example, switches 5, 6, 7 and 8 are provided by MOSFETs. In this example, only switches 5 and 8 are monitored for current levels by current detectors 12, 13, 14 and 15, however, in other embodiments, each switch can have its own respective current detector.

In the example shown in FIG. 13A, the current detectors are shown as voltage comparators (with high gain) placed across each switch. Because the switches have non-zero resistance, a current through them results in a voltage drop across the switch, so a measurement of the voltage is equivalent to measuring the current. Once the current has dropped below a threshold (that can be predetermined and set into the comparator), the switches that were closed are opened. Note that four current detectors are shown in this example, however, this is not necessarily required, and can be determined on a case by case basis per design and required application. For uni-directional power flow (e.g. from left to right, or from PSM to MSM) only one current detector is needed for the Φ1 phase and one for the Φ2 phase. It is also possible to provide the current sensing directly in the two input lines 130 and 140 and to control the opening of the switches when it is sensed that the current falls below the threshold.

For example, a current threshold could be selected to be between about 5% and about 50% of the maximum signal value, including about 10%, about 15%, about 20%, about 25%, about 30%, about 35%, about 40%, about 45% and about 50%. It will be appreciated that these threshold values can be varied to 'tune' the system, depending upon various system parameters such as the level of the signal, the switch resistance and the maximum sensed voltage, as will be understood by the person skilled in the art. In one example, the maximum signal level is about 100 mA, and the switch resistance is about 1 Ohm.

One advantage of the arrangement shown in FIG. 13A is that the timing of the switches (for example the frequency and/or duty cycle) in the PSM 110 can change without the MSM 120 having to receive information relating to the state of the PSM 110.

FIG. 13A also shows comparator 20 between wire 1 and wire 2, and showing current detectors 12, 13, 14 and 15 as having a threshold level prior to triggering. This threshold level can be adjustable.

FIG. 13A also shows second switching circuit 123 with switches 21 and 22, which selectively connect first power storage device 9' to second power storage device 9 to allow transfer of power from the first power storage device 9' to the second power storage device 9 during the second power transfer stage as previously described.

FIG. 13A also shows circuit load R in this example, representing the general circuitry load for the PSM 120 including electrode array 50 (not explicitly shown in this view).

Also shown is switch control block 16, which in this example, contains control logic to control all the switches of all three phases.

Figure 13B:
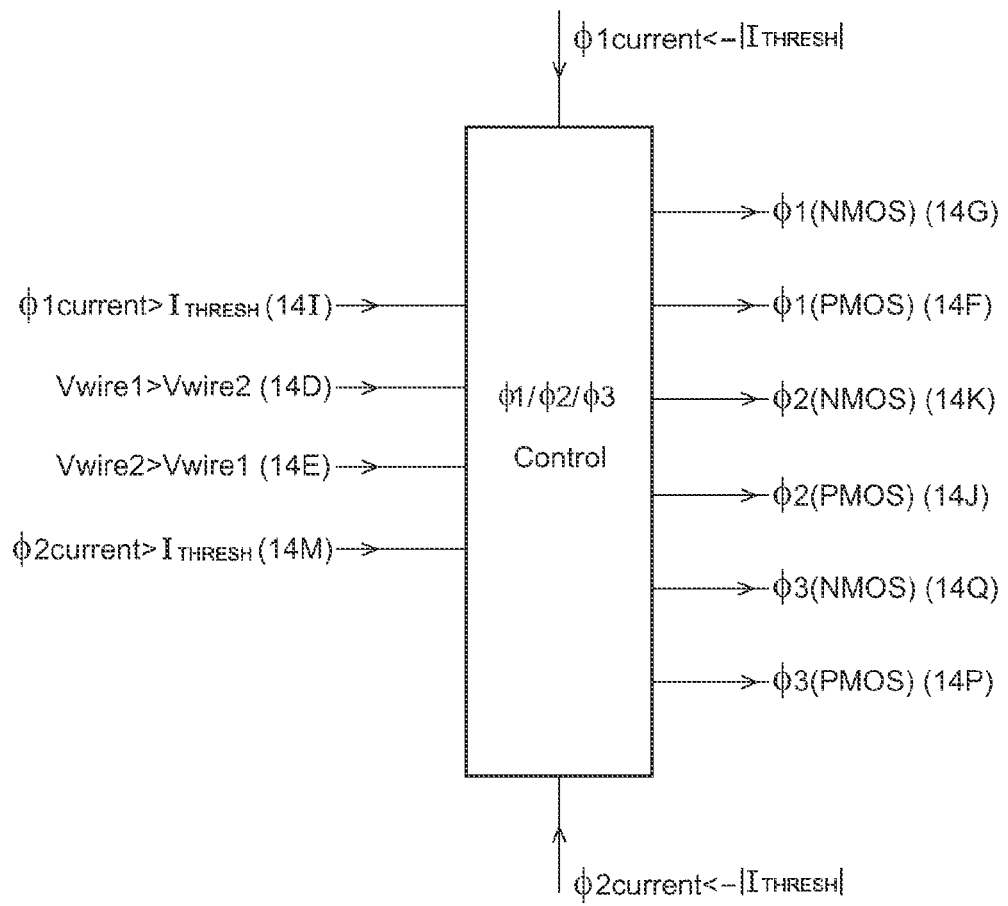
FIG. 13B shows the switch control block of FIG. 13A in more detail.

FIG. 13B shows switch control block 16 in more detail, showing the signal waveforms referred to below with reference to FIGS. 14A to 14R. The function of the control block will be described in more detail below after a description of the relevant waveforms.

Figure 13C:
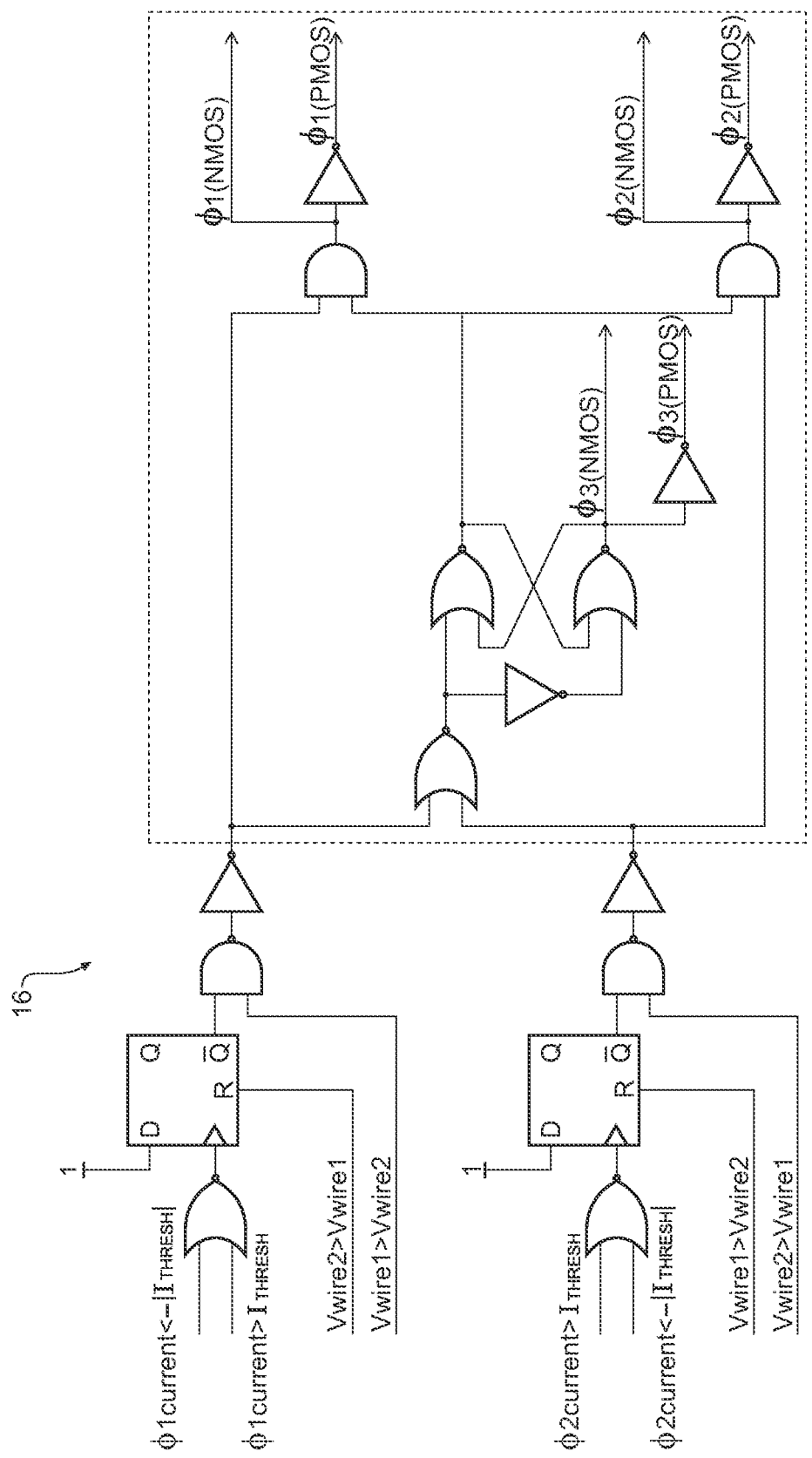
FIG. 13C shows an example logic circuit for the switch control block of FIGS. 13A and 13B.

FIGS. 14A to 14R show various waveforms at different points in the circuit of FIGS. 13A, 13B and 13C.

As can be seen in the various Figures of FIG. 14, when the Φ1 clock goes high, the voltage between Wire1 and Wire2 increases in a finite time, however, in this arrangement, there are no switches closed in the MSM 120, and so there is no negative current spike in the capacitor current. The voltage on the wires goes positive, and the Wire1>Wire2 voltage comparator 18 output goes high, which causes the switch control block 16 to turn on the Φ1 switches 5, 6 in the MSM 120. When these switches turn on, the current through the Φ1 switches 5, 6 spikes up from zero, and gradually decays (note that the capacitor current is the same). Because the switches are resistive, the voltage waveform across the switches is the same as the current. When the current decays below the designated threshold, the voltage comparator 13 on the lower Φ1 switch (Φ1B) goes low (this went high when the current first started flowing, but that edge is not used by the switch control block in this particular application). On this edge, the switch control block 16 will turn off the Φ1 switches 5 and 6. Note that the Φ1 clock in the PSM 110 is still high. When that clock goes low, the Φ1 switches in the PSM 110 are opened, and the voltage on the switches between the two wires is no longer driven by the power source, so it is free to return to zero if any load is present to do so.

FIG. 14A shows the voltage difference between the two wires (130 and 140) as driven by the PSM, with finite rise and fall times.

FIGS. 14B and 14C show the Φ1 and Φ2 clocking signals in the PSM (when acting as master). There is a non-overlapping period.

FIG. 14D shows the output of the comparator (18), which goes high when the wire1 (130) voltage is above the wire2 (140) voltage. The output goes low when the wire1 voltage is below the wire2 voltage.

FIG. 14E shows the output of the comparator (20), which goes high when the wire2 (140) voltage is above the wire1 (130) voltage. The output goes low when the wire2 voltage is below the wire1 voltage.

FIG. 14F shows the gate control voltage that drives the Φ1 PMOS switch (5) in the MSM. When the gate is high, the switch is non-conductive; when it is low, the switch is conductive. This signal is driven by the control logic (16) to go low only after the following events have occurred: the rising edge of the signal in FIG. 14D; the falling edge of the signal in FIG. 14Q; and the rising edge of the signal in FIG. 14P. Then the signal in FIG. 14F is driven by the control logic to go high on the falling edge of the signal in FIG. 14I.

FIG. 14G shows the gate control voltage that drives the Φ1 NMOS switch (6) in the MSM. When the gate is high, the switch is conductive; when it is low, the switch is non-conductive. This signal is driven by the control logic (16) to go high only after the following events have occurred: the rising edge of the signal in FIG. 14D; the falling edge of the signal in FIG. 14Q; and the rising edge of the signal in FIG. 14P. Then the signal in FIG. 14G is driven by the control logic to go low on the falling edge of the signal in FIG. 14I.

FIG. 14H shows an approximation of the current flowing in the Φ1 switches in the MSM. The case shown is when power is flowing in the direction from PSM to MSM. During the period when the Φ1 switches are closed (i.e. as determined by the signals in FIGS. 14F and 14G), there is a positive current flowing from the PSM to MSM. There is an initial spike that decays away towards zero. This drops to zero when the Φ1 switches are opened.

FIG. 14I shows the output of the comparator (13), which effectively amounts to a signal used by the control logic (16) to determine when the Φ1 current is greater than a pre-determined threshold. It is the falling edge of this signal that the control logic will use to determine when to open the Φ1 switches. (Note that the opposite version of this signal, i.e. the output from comparator 12 would be used in the case that power flows from MSM to PSM).

FIG. 14J shows the gate control signal that drives the Φ2 PMOS switch (7) in the MSM. When the gate is high, the switch is non-conductive; when it is low, the switch is conductive. This signal is driven by the control logic (16) to go low only after the following events have occurred: the rising edge of the signal in FIG. 14E; the falling edge of the signal in FIG. 14Q; and the rising edge of the signal in FIG. 14P. Then the signal in FIG. 14J is driven by the control logic to go high on the falling edge of the signal in FIG. 14M.

FIG. 14K shows the gate control voltage that drives the Φ2 NMOS switch (8) in the MSM. When the gate is high, the switch is conductive; when it is low, the switch is non-conductive. This signal is driven by the control logic (16) to go high only after the following events have occurred: the rising edge of the signal in FIG. 14E; the falling edge of the signal in FIG. 14Q; and the rising edge of the signal in FIG. 14P. Then the signal in FIG. 14K is driven by the control logic to go low on the falling edge of the signal in FIG. 14M.

FIG. 14L shows an approximation of the current flowing in the Φ2 switches in the MSM. The case shown is when power is flowing in the direction from PSM to MSM. During the period when the Φ2 switches are closed (i.e. as determined by the signals in FIGS. 14J and 14K), there is a positive current flowing from the PSM to MSM. There is an initial spike that decays away towards zero. This drops to zero when the Φ2 switches are opened.

FIG. 14M shows the output of the comparator (15), which effectively amounts to a signal used by the control logic (17) to determine when the Φ2 current is greater than a pre-determined threshold. It is the falling edge of this signal that the control logic will use to determine when to open the Φ2 switches. (Note that the opposite version of this signal, i.e. the output from comparator 14 would be used in the case that power flows from MSM to PSM).

FIG. 14N shows the current in the first power storage device or capacitor 9' of the MSM. This amounts to a summation of the two current waveforms in FIGS. 14H and 14L during the Φ1 and Φ2 stages.

FIG. 14O shows the voltage stored on the first power storage device or capacitor 9' in the MSM. The voltage charges up during the periods that the Φ1 or Φ2 switches are conducting, and discharges the rest of the time due to the load current drawn from the rest of the circuitry in the MSM (represented by load R). Without the arrangement hereindescribed, there would also be a slight negative transient whenever the polarity of voltage between the wires changes (reflecting a reduced efficiency).

FIG. 14P shows the gate control voltage that drives the Φ3 PMOS switch 21 in the MSM. When the gate is high, the switch is non-conductive; when it is low, the switch is conductive. This signal goes high after the rising edges of FIGS. 14D and 14E, but before the relevant edges of FIGS. 14F, 14G, 14J and 14K. Similarly, the signal goes low after the relevant edges of FIGS. 14F, 14G, 14J and 14K. This guarantees that there is no overlapping time where both the Φ3 and Φ1/Φ2 switches are closed FIG. 14Q shows the gate control voltage that drives the Φ3 NMOS switch 22 in the MSM. When the gate is high, the switch is conductive; when it is low, the switch is non-conductive. This signal goes low after the rising edges of FIGS. 14D and 14E, but before the relevant edges of FIGS. 14F, 14G, 14J and 14K. Similarly, the signal goes high after the relevant edges of FIGS. 14F, 14G, 14J and 14K.

FIG. 14R shows the voltage across the second power storage device or capacitor 9 as it is charged via switches 21 and 22 during the second power transfer stage. As can be seen, the device charges when each of the Φ3 switches 21, 22 are conducting. During the first power transfer stage, when both Φ3 switches are non-conducting, the voltage magnitude of the second power storage device 9 remains substantially constant, unless, it is being discharged through being drawn on by load R during this time, as illustrated in FIG. 14R.

As can be seen in the capacitor current waveform, ICAPACITOR in FIG. 14P, the current is always positive, which means that the voltage across the capacitor 9' keeps building when the capacitor current is non-zero, up to a maximum constant voltage. The voltage reduces as current is transferred to the second power storage device or capacitor 9 during the second power transfer stage, but is constantly replenished by the charging function described above during the first power transfer stage. At no time does the capacitor 9' discharge back to the PSM as in prior art arrangements, thus providing a highly-efficient power charging circuit.

Returning now to FIG. 13B, showing switch control block 16, FIG. 13C shows an example of a suitable logic circuit to provide the functional control to control switches 5, 6, 7, 8, 21 and 22 in accordance with the waveforms of FIG. 14 described above.

While FIGS. 13A, 13B and 13C show switch control block 16 as a single block, it will be appreciated that each of the phases Φ1, Φ2 and Φ3 can have their own switch control blocks, or indeed, in any combination.

Figure 15:
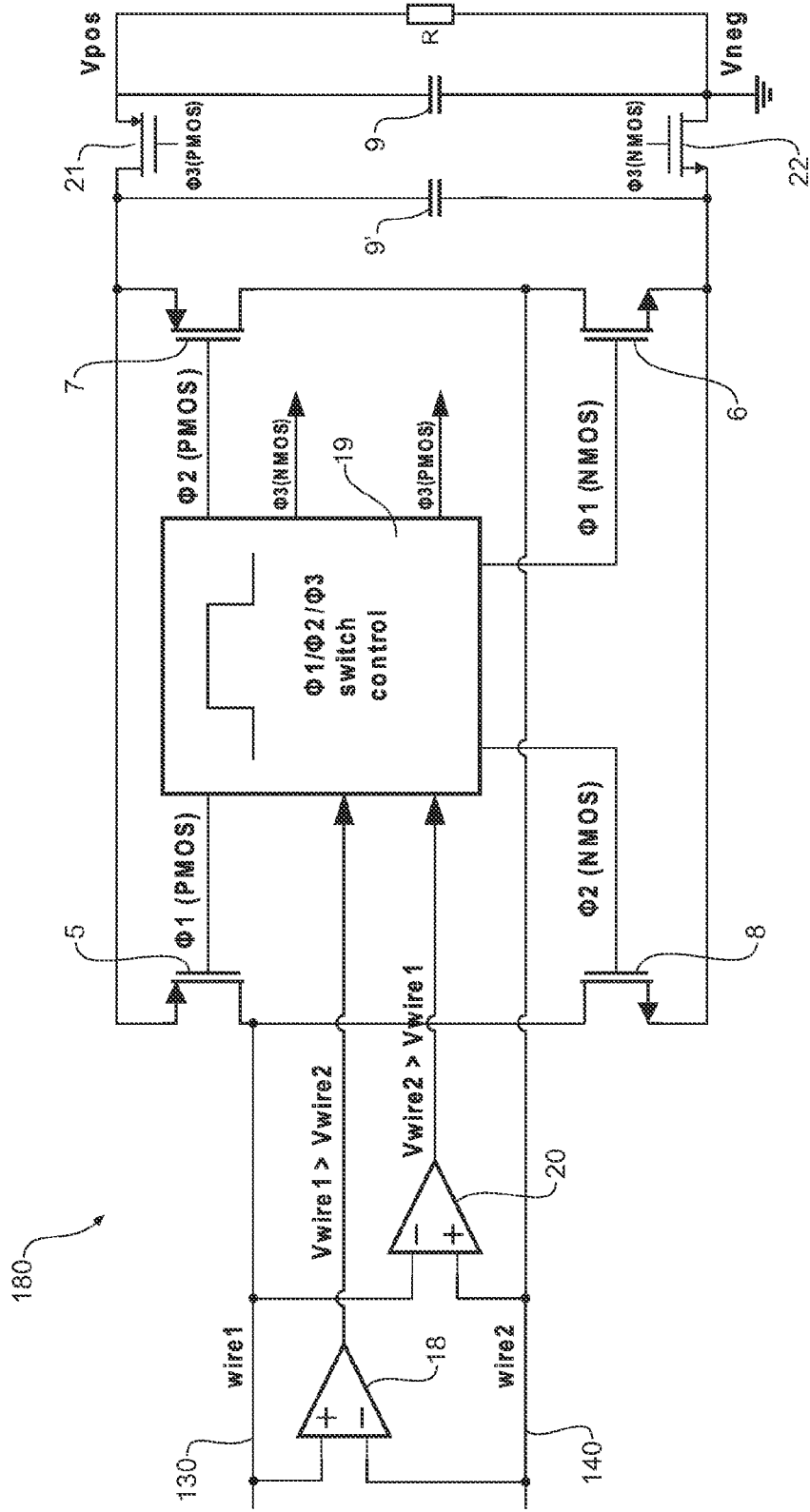
FIG. 15 shows a circuit in which the opening of the switches is controlled according to timing.
Figure 16:
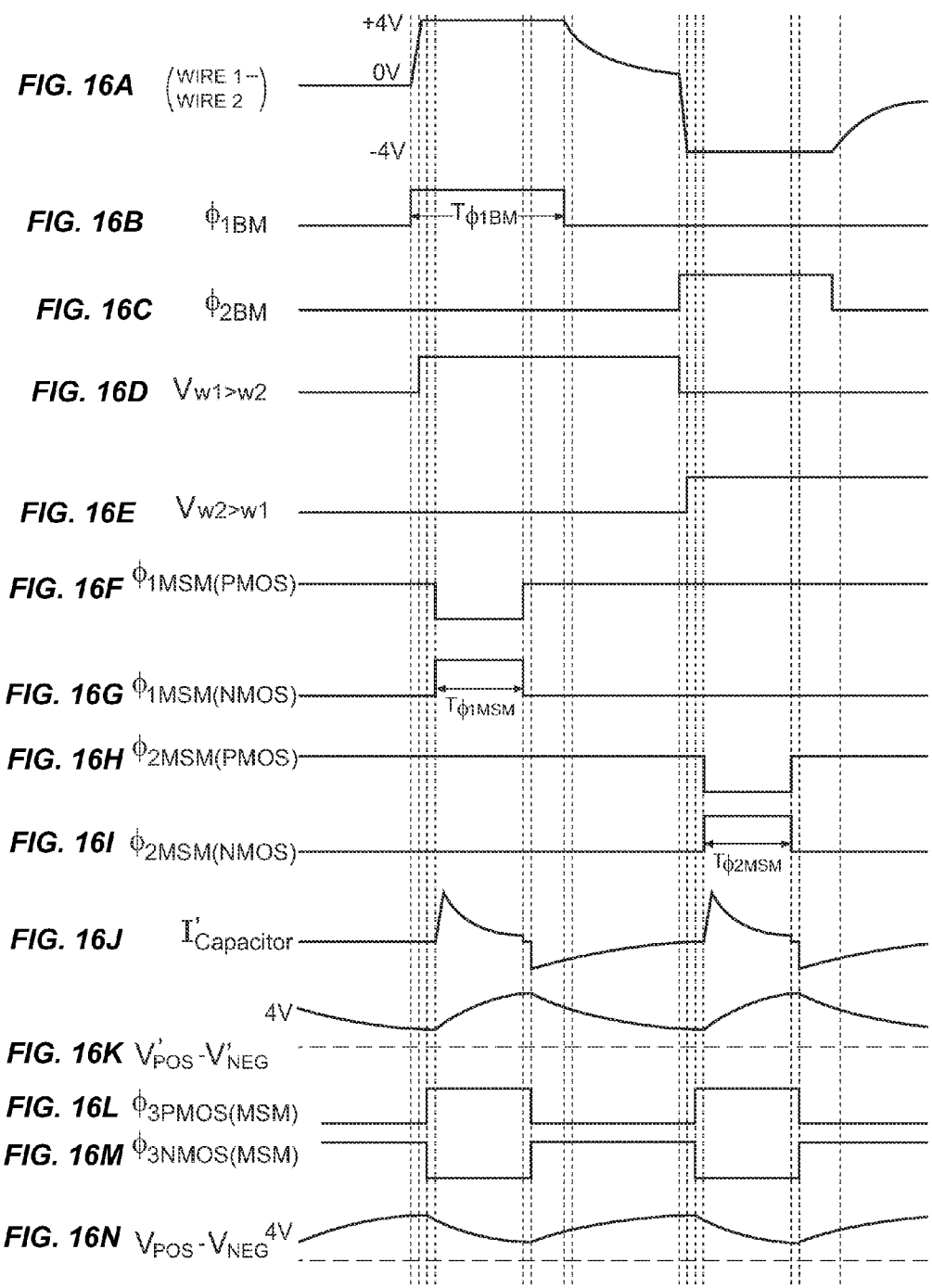
FIG. 16A shows a waveform of a signal on the two wires in the arrangement of FIG. 15.
FIG. 16B shows a waveform of the Φ1 clocking signal in the PSM of FIG. 15.
FIG. 16C shows a waveform of the Φ2 clocking signal in the PSM of FIG. 15.
FIG. 16D shows the output of the comparator 18 in FIG. 15.
FIG. 16E shows the output of the comparator 20 in FIG. 15.
FIG. 16F shows the gate control voltage driving switch 5 in the MSM in FIG. 15A.
FIG. 16G shows the gate control voltage driving switch 6 in the MSM in FIG. 15A.
FIG. 16H shows the gate control voltage that drives the Φ2 PMOS switch 7 in the MSM in FIG. 15.
FIG. 16I shows the gate control voltage that drives the Φ2 NMOS switch 8 in the MSM in FIG. 15.
FIG. 16J shows the current in the storage capacitor 9' of the MSM in FIG. 15.
FIG. 16K shows the voltage stored on the storage capacitor 9' in the MSM FIG. 15.
FIG. 16L shows the gate control voltage that drives the Φ3 PMOS switch in the MSM in FIG. 15.
FIG. 16M shows the gate control voltage that drives the Φ3 NMOS switch in the MSM in FIG. 15.
FIG. 16N shows the voltage across the storage capacitor 9 of the MSM in FIG. 15.

In another embodiment, the switching of the switches in the MSM 120 is controlled by a clock, synchronised with the switches in the PSM. FIG. 15 shows a circuit block diagram of a circuit according to this embodiment. Shown are switches 5, 6, 7 and 8, voltage comparator 18 between lines 130 and 140, and first power storage device or capacitor 9', as previously described with reference to FIG. 13A. It will be noted however that in this embodiment, no current detectors for the switches are required. Instead of using low-current detectors to determine when to open the switches, a timeout period is employed. For example, when the wire voltage changes from negative to positive, the Φ1 switches will be closed in the MSM in response to this, as before. However, instead of using either the voltage, or a low-current detector, the switches automatically open after a predetermined time. This period should be shorter than the time taken for the voltage on the wires to change in polarity again, hence the efficiency is maximised.

The clocking of the switches in the PSM has not changed (still an independent clock), whilst the clocking of the switches in MSM is different from the previous method described with reference to FIGS. 13A, 13B, 13C and 14. In this arrangement, when the voltage difference between wire1 and wire2 goes positive, the Φ1 clock in MSM is caused to go high (for an NMOS switch) (low for the PMOS switch). This stays high for a pre-determined timeout period and then goes low again (or high for the PMOS switch). The timeout period can be generated either by a one-shot circuit or a counter driven by a higher frequency clock. This can be provided as a separate circuit or can be provided as part of switch control 19. It will be noted that this period is designed to be shorter than the Φ1 period in the PSM. This can be a fixed value that takes into account the error of the timeout period with respect to that in the PSM. For example, if the PSM Φ1 period is 10 us and the relative error between this and the one-shot circuit in MSM is 10%, then a Φ1 timeout of 8us in PSM could be chosen for correct operation.

The same occurs for Φ2. The result is that there is no negative (discharging) current flowing in the capacitor 9', thereby avoiding the reduction in efficiency that would otherwise occur.

Also shown in FIG. 15 are switches 21 and 22 and second power storage device or capacitor 9, for providing power to load R.

FIGS. 16A to 16N illustrate various waveforms at the points described above in relation to FIG. 15. Again, as with FIG. 14N, it can be seen that the current ICAPACITOR (FIG. 16I) in the first power storage device or capacitor 9' is never negative during the Φ1 and Φ2 stages, only in the Φ3 stage.

FIG. 16A shows the voltage difference between the two wires (130 and 140) as driven by the PSM, with finite rise and fall times.

FIGS. 16B and 16C show the Φ1 and Φ2 clocking signals in the PSM (when acting as master). There is a non-overlapping period in this example.

FIG. 16D shows the output of the comparator (18), which goes high when the wire1 (130) voltage is above the wire2 (140) voltage. The output goes low when the wire1 voltage is below the wire2 voltage.

FIG. 16E shows the output of the comparator (20), which goes high when the wire2 (140) voltage is above the wire1 (130) voltage. It goes low when the wire2 voltage is below the wire1 voltage.

FIGS. 16F and 17G are used for the same purpose as those described in FIGS. 14F and 14G respectively, however their means of generation is different. The rising edge of the gate control for Φ1 NMOS switch (falling edge for gate control of Φ1 PMOS switch) is still caused by the control logic (19) to occur after the rising edge of the signal in FIG. 16D and once the signal in FIG. 16M has gone low and the signal in FIG. 16L has gone high. However, the falling edge of the gate control for Φ1 NMOS switch (rising edge for gate control of Φ1 PMOS switch) is caused by a timing mechanism within the control logic (19). For example, when the timer reaches the preset timeout of for example, 8 us.

FIGS. 16H and 16I are used for the same purpose as those described in FIGS. 14J and 14K respectively, however their means of generation is different. The rising edge of the gate control for Φ2 NMOS switch (falling edge for gate control of Φ2 PMOS switch) is still caused by the control logic (19) to occur after the rising edge of the signal in FIG. 16E and once the signal in FIG. 16M has gone low and the signal in FIG. 16L has gone high. However, the falling edge of the gate control for Φ2 NMOS switch (rising edge for gate control of Φ2 PMOS switch) is caused by a timing mechanism within the control logic (19).

FIG. 16J is the same as FIG. 14N, although the duration is not necessarily identical.

FIG. 16K shows the voltage stored on the storage capacitor 9' in the MSM. The voltage charges up during the periods that the Φ1 or Φ2 switches are conducting (during the first power transfer stage), and discharges when the Φ3 switches are conducting, during the second power transfer stage. Without the arrangement described herein, there would also be a slight negative transient whenever the polarity of voltage between the wires changes (reflecting a lower efficiency in power transfer).

FIGS. 16L and 16M show the gate control for the switches 21 and 22 to provide for the second power transfer stage to transfer power from the first power storage device 9' to the second power storage device 9.

FIG. 16N shows the voltage across the second power storage device 9 as it is charged during the second power transfer stage from the first power storage device 9'. During the periods where the Φ3 switches 21, 22 are not conducting, the voltage across the second power storage device 9 remains substantially constant, or, if being drawn on by the load R, will discharge slightly until it is recharged during the next second power transfer stage.

In a further alternative, the one-shot circuit can be made programmable and if a data link is available between the two modules 110, 120, then information about the switching frequency could be sent from PSM 110 to MSM 120 to improve the range of frequencies over which the system could operate.

If the pulse width or switching frequency of the switches in the PSM is variable, this can be addressed by the use of an algorithm in the Φ1/Φ2 switch control block 19 in the MSM 120 to learn what the timeout period or a predetermined time, needs to be, by observing the voltage on the wires over a switching cycle, and adjusting the timeout accordingly.

For example, there could be provided a higher frequency clock in the MSM 120 (at least 10× the switching frequency of the PSM 110) which can be used to count the number of cycles used for the Φ1 and Φ2 pulse widths (via the two voltage comparators 18, 20). For example, if the MSM 120 counts that the Φ1 pulse width is 10 cycles, then in the next cycle it will only keep the Φ1 switches in MSM 120 closed for 9 cycles and then open them. In this way, there is only an error of 10% and will still provide the advantages of the arrangements described even if the PSM 110 changes frequency (or even just duty cycle). The same applies to Φ2.

The above has described various embodiments for providing transfer of power from one module to another, using a rectification circuit having high efficiency. It will be understood that many variations and modifications are possible. For example, as previously described, the various aspects will also work if power flows from the MSM to the PSM (this would imply that a source of power is present in the MSM).

That is, power can flow bidirectionally in this arrangement. Secondly, it is not necessary that the PSM be the Master. That is, the MSM could be the Master with autonomous control over its own switches, whilst the PSM could be the Slave with the appropriate switch control circuitry as described previously. This distinction can be made regardless of the direction of power flow.

Furthermore, for the current detector method of determining when to open the switches in the slave module, the current detection does not need to be limited to detecting the current directly in one (or more) of the switches. It could detect the current flowing in a device in series with the switches.

Other current detection mechanisms could also be used, instead of the voltage comparators across resistive switches shown in FIG. 13A. Examples include a hall-effect sensor in series with the switches, or an inductive element in series.

Figure 17:
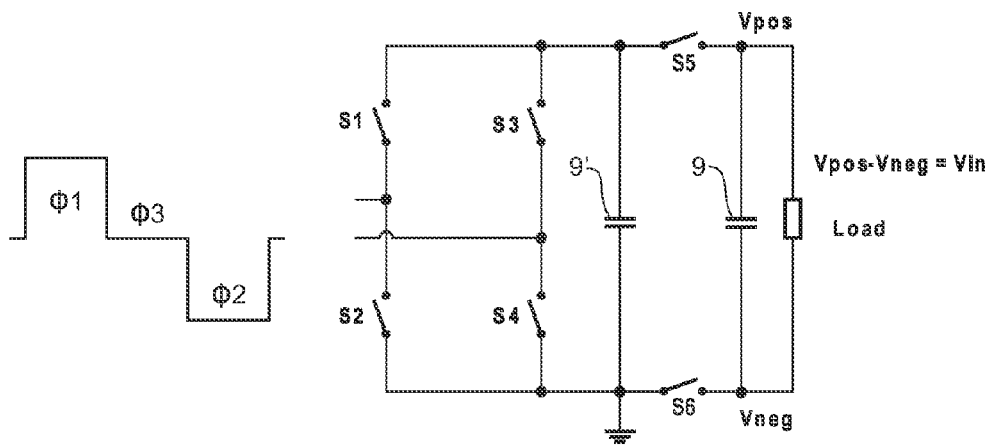
FIG. 17 shows an arrangement for a two wire interface circuit with four switches.

Following, various different embodiments and variations are described, with reference to FIGS. 17 to 20. FIG. 17 shows a generalised slave module (which could be either the PSM 110 or MSM 120) having a four-switch configuration. Also shown in FIG. 17 is a general waveform of the signal on the wires 130, 140, generated by the master module (which could be the other of the MSM 120 or MSM 110). While in previous examples, it has been shown that this waveform can be generated by a similar four-switch arrangement in the master module, as shown in FIG. 12, it will be appreciated that in some embodiments, this waveform can be generated by any suitable means including a standard waveform generator, whether by analogue circuit arrangement and/or digital circuit arrangement.

As previously described, in the four-switch arrangement, switches S1 and S4 are closed during Φ1, and switches S2 and S3 are closed during Φ2. This configuration can be used in certain arrangements such as a capacitively coupled link (as in the arrangement of FIG. 12), or a transformer coupled link. Also shown are the Φ3 switches S5 and S6, for selectively connecting the second power storage device 9 to the first power storage device 9', which in both cases in this example are capacitors.

Figure 18:
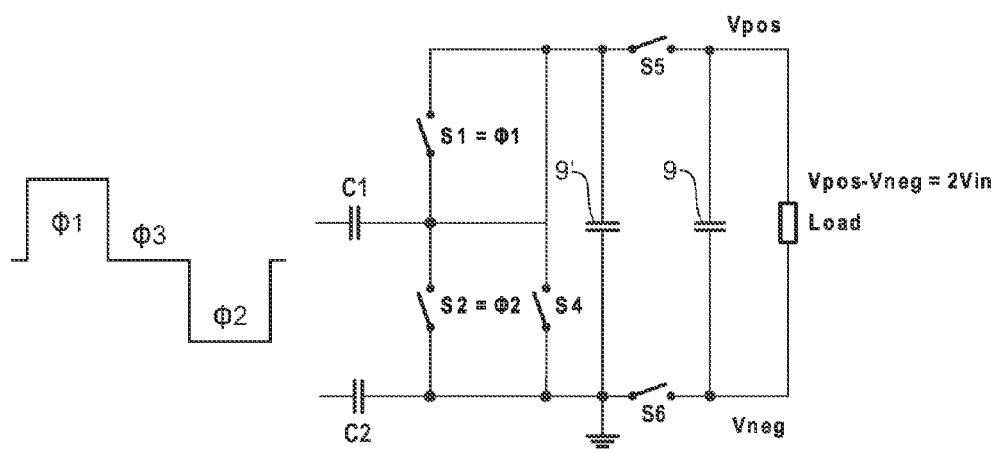
FIG. 18 shows a two wire interface with two switches that provides for voltage doubling.

FIG. 18 shows a two-switch topology, which also acts as a voltage doubler, with capacitors C1 and C2 involved in the voltage doubling. In this arrangement, switch S1 is closed during Φ1, switch S2 is closed during Φ2, switch S3 is permanently open or does is non-existent and switch S4 is permanently closed or replaced by a short circuit.

In operation, each capacitor C1 and C2 charges up during Φ2, and then this voltage is added to the source voltage during Φ1, providing twice the voltage of the source voltage on the storage device or capacitor 9' (in this example). For example, if the source voltage is about 4V, the voltage across first power storage device or capacitor 9' will be about 8V. It will be appreciated that other arrangements providing further voltage multiplication (e.g. tripler or quadrupler) are also possible. Also shown are the Φ3 switches S5 and S6, for selectively connecting the second power storage device 9 to the first power storage device 9', which in both cases in this example are capacitors.

It will be appreciated that these various arrangements can be provided by either providing four switches and providing appropriate control signals to keep them closed or open as required to provide the required number of switches, or can be provided by manufacturing the circuit with the required number of switches and open/closed circuits.

Figure 19:
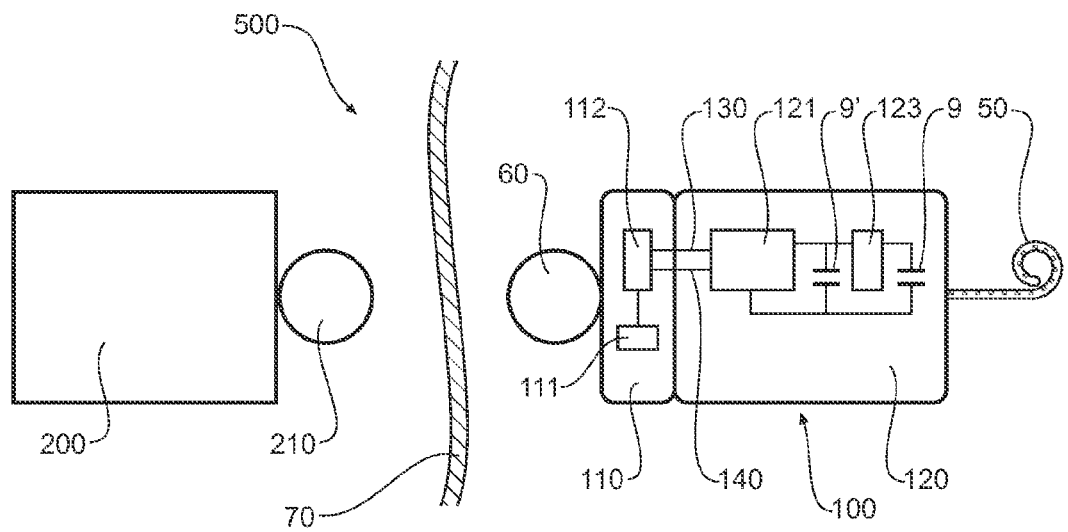
FIG. 19 shows a medical implant system corresponding to a cochlear implant system including an external component and an internal component.

FIG. 19 shows a medical implant system, in this case a cochlear implant system 500, having an external component 200, being a sound processor, and an internal component 100 or medical implant, in this case, being a stimulator, implanted into an implantee (not shown), under tissue 70.

In operation, processor 200 receives input signals in the form of sound information from the surrounding area around the implantee via any suitable means, such as a microphone (not shown) and processes this data into control signals for transmission to the internal component or stimulator 100. The control signals are transmitted transcutaneously across tissue 70 via transmitting coil 210, to be received by receiving coil 60 of the internal component. The control signals are then further processed by the circuitry in the stimulator 100 to provide stimulation signals for applying directly to the cochlea of the implantee via electrode array 50 as will be understood by the person skilled in the art.

The circuitry in the stimulator is in this application, powered by the voltage developed across second power storage device 9 (such as a capacitor) as previously described. First power storage device or capacitor 9' is charged in the first power transfer stage by power source or battery 111 in power source module (PSM) 110, via circuitry 112 in the power source module (PSM) 110 and first switching circuit 121 powering first power storage device 9' in the internal component or, in this case, main stimulator module (MSM) 120 and wires 130 and 140 as previously described. Second switching circuit 123 then acts to allow power to transfer from first power storage device 9' to second power storage device 9 during the second power transfer stage. In some embodiments, the transmitted signal from the external component to the internal component or implant can also contain a power element which is extracted in the power source module 110 to recharge power source or battery 111.

In some embodiments, as shown in FIG. 19, first module or power source module 110 can be removed or separated from second module or main stimulator module 120 to enable replacement of battery 111 and then reconnected to main stimulator module 120. This enables a much simpler and less invasive procedure for changing the battery or for performing other maintenance to the power source module. In this aspect or embodiment, the circuit 112 and circuit 121 can be present, but can also be omitted. It will also be appreciated that receive coil 60 can be connected to power source module 110 or to main stimulator module 120.

Figure 20:
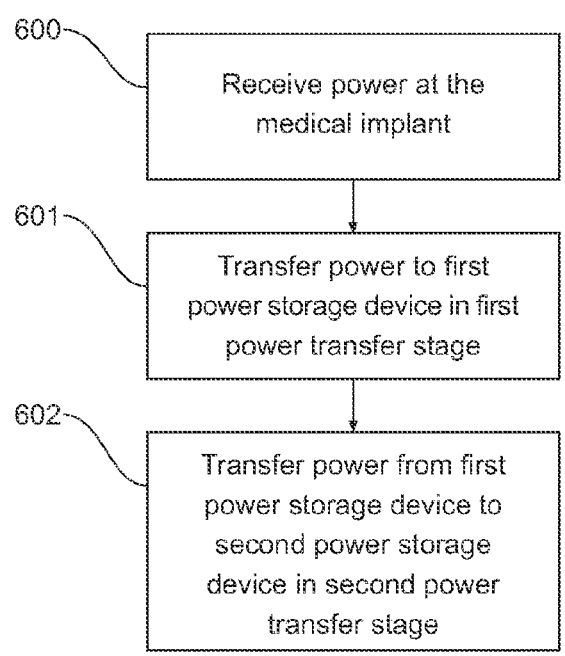
FIG. 20 shows a flowchart of a method of transferring power from a power source to a power storage device.
Figure 21:
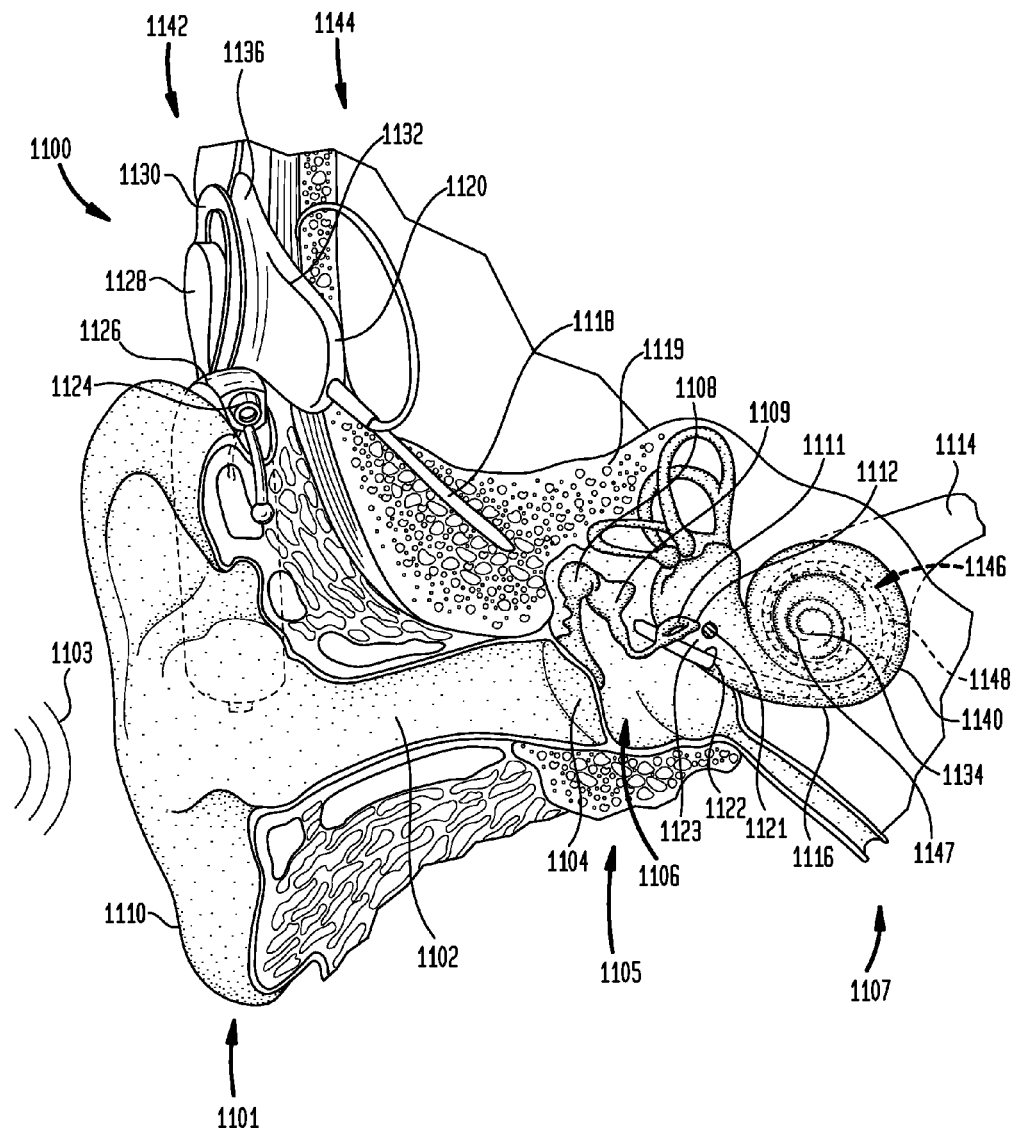
FIG. 21 shows a perspective view of a cochlear implant with which embodiments of the present invention may be implemented.

Also described herein is a method of transferring power between a first medical implant and a second medical implant connected by a wire connection. As shown in FIG. 20, in step 600, power is received on the wire connection at the second medical implant. In step 601, at least a portion of the power is transferred to a first power storage device via a first switching circuit in a first power transfer stage, and then in step 602, at least a portion of the power stored on the first power storage device is transferred to a second power storage device via a second switching circuit in a second power transfer stage. FIG. 21 is perspective view of a cochlear implant, referred to as cochlear implant 1100, implanted in a recipient. The recipient has an outer ear 1101, a middle ear 1105 and an inner ear 1107. Components of outer ear 1101, middle ear 1105 and inner ear 1107 are described below, followed by a description of cochlear implant 1100.

In a fully functional ear, outer ear 1101 comprises an auricle 1110 and an ear canal 1102. An acoustic pressure or sound wave 1103 is collected by auricle 1110 and channeled into and through ear canal 1102. Disposed across the distal end of ear canal 1102 is a tympanic membrane 1104 which vibrates in response to sound wave 1103. This vibration is coupled to oval window or fenestra ovalis 1112 through three bones of middle ear 1105, collectively referred to as the ossicles 1106 and comprising the malleus 1108, the incus 1109 and the stapes 1111. Bones 1108, 1109 and 1111 of middle ear 1105 serve to filter and amplify sound wave 1103, causing oval window 1112 to articulate, or vibrate in response to vibration of tympanic membrane 1104. This vibration sets up waves of fluid motion of the perilymph within cochlea 1140. Such fluid motion, in turn, activates tiny hair cells (not shown) inside of cochlea 1140. Activation of the hair cells causes appropriate nerve impulses to be generated and transferred through the spiral ganglion cells (not shown) and auditory nerve 1114 to the brain (also not shown) where they are perceived as sound.

Cochlear implant 1100 comprises an external component 1142 (which, in some embodiments, corresponds to external component 200 detailed above with respect to FIG. 19) which is directly or indirectly attached to the body of the recipient, and an internal component 1144 (which, in some embodiments, corresponds to the internal component 100 detailed above with respect to FIG. 19) which is temporarily or permanently implanted in the recipient. External component 1142 typically comprises one or more sound input elements, such as microphone 1124 for detecting sound, a sound processor 1126, a power source, such as a battery for example (not shown), and an external transmitter unit 1128. External transmitter unit 1128 comprises an external coil 1130 and, preferably, a magnet (not shown) secured directly or indirectly to external coil 1130. Sound processor 1126 processes the output of microphone 1124 that is positioned, in the depicted embodiment, by auricle 1110 of the recipient. Sound processor 1126 generates encoded signals, sometimes referred to herein as encoded data signals, which are provided to external transmitter unit 1128 via a cable (not shown). Sound processor 1126 may further comprise a data input interface (not shown) that may be used to connect sound processor 1126 to a data source, such as a personal computer or musical instrument (e.g., a MIDI instrument).

Internal component 1144 comprises an internal receiver unit 1132, a stimulator unit 1120, and a stimulating lead assembly 1118. Internal receiver unit 1132 comprises an internal coil 1136, and preferably, a magnet (also not shown) fixed relative to the internal coil. Internal receiver unit 1132 and stimulator unit 1120 (which, in some embodiments, corresponds to the stimulator discussed above) are hermetically sealed within separate or shared biocompatible housings, sometimes collectively referred to as a stimulator/receiver unit. In an exemplary embodiment, an implantable power source in a module separate from the stimulator unit (e.g., the internal receiver unit 1132) and/or the stimulator/receiver unit provides power to these units via an electrical connection corresponding to that detailed above. The internal coil receives stimulation data and/or power from external coil 1130. Stimulating lead assembly 1118 has a proximal end connected to stimulator unit 1120, and a distal end implanted in cochlea 1140. Stimulating lead assembly 1118 extends from stimulator unit 1120 to cochlea 1140 through mastoid bone 1119. In some embodiments stimulating lead assembly 1118 may be implanted at least in basal region 1116, and sometimes further. For example, stimulating lead assembly 1118 may extend towards apical end of cochlea 1140, referred to as cochlea apex 1134. In certain circumstances, stimulating lead assembly 1118 may be inserted into cochlea 1140 via a cochleostomy 1122. In other circumstances, a cochleostomy may be formed through round window 1121, oval window 1112, the promontory 1123 or through an apical turn 1147 of cochlea 1140.

Stimulating lead assembly 1118 comprises a longitudinally aligned and distally extending array 1146 of electrode contacts 1148, sometimes referred to as array of electrode contacts 1146 herein. Although array of electrode contacts 1146 may be disposed on stimulating lead assembly 1118, in most practical applications, array of electrode contacts 1146 is integrated into stimulating lead assembly 1118. As such, array of electrode contacts 1146 is referred to herein as being disposed in stimulating lead assembly 1118. Stimulator unit 1120 generates stimulation signals which are applied by electrode contacts 1148 to cochlea 1140, thereby stimulating auditory nerve 1114. Because, in cochlear implant 1100, stimulating lead assembly 1118 provides stimulation, stimulating lead assembly 1118 is sometimes referred to as a stimulating lead assembly.

In cochlear implant 1100, external coil 1130 transmits electrical signals (that is, power and stimulation data) to internal coil 1136 via a radio frequency (RF) link. Internal coil 1136 is typically a wire antenna coil comprised of multiple turns of electrically insulated single-strand or multi-strand platinum or gold wire. The electrical insulation of internal coil 1136 is provided by a flexible silicone moulding (not shown). In use, implantable receiver unit 1132 may be positioned in a recess of the temporal bone adjacent auricle 1110 of the recipient.

While the various aspects have been described with reference to specific embodiments, it will be appreciated that many variations and modifications may be made.

Furthermore, while the various aspects herein have been described with specific reference to a cochlear implant, it will be understood that the principles of the various aspects can be applied to other types of medical implants. For example:

ABI (Auditory Brainstem Implant, electrode for hearing, placed in the brainstem) such as Cochlear Corporation's NUCLEUS 24® Multichannel Auditory Brainstem Implant (Multichannel ABI).

The auditory brainstem implant consists of a small electrode that is applied to the brainstem where it stimulates acoustic nerves by means of electrical signals. The stimulating electrical signals are provided by a signal processor processing input sounds from a microphone located externally to the user. This allows the user to hear a certain degree of sound.

FES (Functional Electrical Stimulation). FES is a technique that uses electrical currents to activate muscles and/or nerves, restoring function in people with paralysis-related disabilities.

Injuries to the spinal cord interfere with electrical signals between the brain and the muscles, which can result in paralysis.

SCS (Spinal Cord Stimulator). This system delivers pulses of electrical energy via an electrode in the spinal area and can be used for pain management. An example of a commercially available system is the RESTOREPRIME system by Medtronic, Inc, USA.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

As may be understood from the above, in a exemplary embodiment of the present invention, there is a medical implant that includes a first and second power storage device and respective first and second switching circuits. In use, the first switching circuit transfers power to the first power storage device in a first power transfer stage, and the second switching circuit transfers power from the first power storage device to the second power storage device in a second power transfer stage.

In an exemplary embodiment, the first and second switching circuits are not conductive at the same time.

In another exemplary embodiment of the present invention, there is a medical implant system that comprises a first and second medical implant connected via a connection, which in one form, is a two wire connection. There is a power storage device in the first implant for providing power to first and second power storage devices in the second implant. The second implant is also provided with respective first and second switching circuits to allow transfer of power from the first implant to the first and second power storage devices in the second implant. In some embodiments, this medical implant system is a cochlear implant system.

In another embodiment of the present invention, there is a method of transferring power from a first medical implant to a second medical implant. The method comprises switching power through a first switching circuit to a first power storage device in the second implant and then connecting the second power storage device via the second switching circuit to transfer power to the second power storage device.

In another embodiment of the present invention, there is a medical implant comprising a first power storage device, a first switching circuit for receiving and transferring power from an implant connector to the first power storage device in a first power transfer stage, a second power storage device, and a second switching circuit for transferring power from the first power storage device to the second power storage device in a second power transfer stage. In another embodiment, there is a medical implant as detailed above and/or below, wherein the second switching circuit is not conductive when the first switching circuit is conductive and the first switching circuit is not conductive when the second switching circuit is conductive. In another embodiment, there is a medical implant as detailed above and/or below, wherein the implant connection is a two-wire connection for carrying a signal comprising at least a power component.

In another embodiment, there is a medical implant as detailed above and/or below, wherein the first switching circuit is conductive in a first and second phase of the signal and the second switching circuit is conductive in a third phase of the signal. In another embodiment, there is a medical implant as detailed above and/or below, wherein the first switching circuit comprises four switches. In another embodiment, there is a medical implant as detailed above and/or below, the second switching circuit comprises two switches. In another embodiment, there is a medical implant as detailed above and/or below, wherein the first power storage device is a capacitor.

In another embodiment, there is a medical implant as detailed above and/or below, wherein the second power storage device is a capacitor. In another embodiment, there is a medical implant as detailed above and/or below, wherein the implant connection comprises decoupling capacitors. In another embodiment, there is a medical implant as detailed above and/or below, wherein the medical implant is a cochlear implant.

In another embodiment, there is a medical implant system, comprising a first medical implant connected to a second medical implant via a connection, the first medical implant comprising a first power storage device, a power storage interface for connecting the first power storage device to the connection, the second medical implant comprising a first power storage device, a first switching circuit for receiving and transferring power from an implant connection to the first power storage device in a first power transfer stage, a second power storage device, and a second switching circuit for transferring power from the first power storage device to the second power storage device in a second power transfer stage.

In another embodiment, there is a medical implant system as detailed above and/or below, wherein the medical implant system is a cochlear implant system. In another embodiment, there is a medical implant system as detailed above and/or below, wherein the first medical implant is a power module and the second medical implant is a stimulator module. In another embodiment, there is a medical implant system as detailed above and/or below, further comprising an external module. In another embodiment, there is a medical implant system as detailed above and/or below, wherein the external module is a processor. In another embodiment, there is a medical implant system as detailed above and/or below, wherein the connection is a wire connection.

In another embodiment of the present invention, there is a method of transferring power between a first medical implant and a second medical implant connected by a connection, the method comprising receiving the power via the connection at the second medical implant, transferring at least a portion of the power to a first power storage device via a first switching circuit in a first power transfer stage, and transferring at least a portion of the power stored on the first power storage device to a second power storage device via a second switching circuit in a second power transfer stage. In another embodiment of the present invention, there is a method as described above and/or below, wherein the step of transferring the at least a portion of the power via the connection to the first power storage device is performed when the first switching circuit is conducting and the second switching circuit is not conducting. In another embodiment of the present invention, there is a method as described above and/or below, wherein the step of transferring the at least a portion of the power stored on the first power storage device to the second power storage device is performed when the first switching circuit is not conducting and the second switching circuit is conducting.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:
1. A medical implant comprising:
a first power storage device;
a first switching circuit configured to receive power from a power source of the medical implant via an implant connector electrically connected to the medical implant and transfer the received power to the first power storage device in a first power transfer stage;
a second power storage device; and
a second switching circuit configured to:
electrically isolate the first power storage device from tissue of a recipient of the medical implant during the first power transfer stage; and
transfer power from the first power storage device to the second power storage device in a second power transfer stage, wherein the first switching circuit is further configured to electrically isolate the first and second power storage devices from the implant connector during the second power transfer stage.

2. A medical implant as claimed in claim 1, further comprising:
a switching circuit control system configured to:
control the first and second switching circuits so that the first and second power storage devices are electrically isolated from the implant connector when the first power storage device is electrically connected to the second power storage device during the second power transfer stage; and
control the first and second switching circuits so that the first power storage device is electrically isolated from the second power storage device when the first power storage device is electrically connected to the implant connector during the first power transfer stage.

3. A medical implant as claimed in claim 1 wherein:
the second switching circuit is non-conductive when the first switching circuit is conductive and the first switching circuit is non-conductive when the second switching circuit is conductive.

4. A medical implant as claimed in claim 3 wherein:
the implant connector is a two-wire connection for carrying a signal comprising at least a power component.

5. A medical implant as claimed in claim 4 wherein:
the first switching circuit is conductive during the first power transfer stage in a first and second phase of the signal; and
the second switching circuit is conductive during the second power transfer stage in a third phase of the signal.

6. A medical implant as claimed in claim 4 wherein:
the first switching circuit comprises four switches; and
the second switching circuit comprises two switches.

7. A medical implant as claimed in claim 6 wherein:
the first power storage device is a capacitor; and
the second power storage device is a capacitor.

8. A medical implant as claimed in claim 1, further comprising:
a switching circuit control system configured to:
control the first and second switching circuits so that the second power storage device is charged with power delivered to the first power storage device from the power source of the medical implant via the implant connector without the second power storage device being electrically connected to the implant connector.

9. A medical implant as claimed in claim 4 wherein:
the implant connector includes decoupling capacitors electrically connected to the first switching circuit.

10. A medical implant as claimed in claim 1, wherein:
the medical implant is a stimulator, or a receiver/stimulator of a cochlear implant.

11. A cochlear implant comprising:
a power source;
an implant connector;
a first power storage device;
a first switching circuit configured to transfer power from the power source to the first power storage device via the implant connector during a first power transfer stage;
a second power storage device;
a second switching circuit configured to transfer power from the first power storage device to the second power storage device during a second power transfer stage; and
a switching circuit control system configured to control the first and second switching circuits so that:
the first power storage device is electrically isolated from the second power storage device and tissue of a recipient of the cochlear implant during the first power transfer stage when the first power storage device is electrically connected to the power source via the implant connector; and
each of the first and second power storage devices is electrically isolated from the implant connector and the power source during the second power transfer stage when the first power storage device is electrically connected to the second power storage device.

12. The cochlear implant of claim 11, wherein the switching circuit control system is further configured to control:
the first switching circuit to be conductive when the second switching circuit is non-conductive;
the first switching circuit to be conductive during the first power transfer stage; and
the second switching circuit to be conductive during the second power transfer stage.

13. The cochlear implant of claim 11, wherein the power source is a battery.

14. A method for transferring power between first and second power storage devices of a cochlear implant having first and second switching circuits, the method comprising:
receiving power from a power source of the medical implant via an implant connector electrically connected to the first switching circuit;
charging the first power storage device by transferring the received power to the first power storage device via the first switching circuit; and
transferring, via the second switching circuit, power from the first power storage device to the second power storage device during a second power transfer stage.

15. The method of claim 14, further comprising:
controlling the first and second switching circuits so that:
the first power storage device is electrically isolated from the second power storage device and tissue of a recipient of the cochlear implant during the first power transfer stage when the first power storage device is electrically connected to the power source via the implant connector; and
the first and second power storage devices are electrically isolated from the implant connector during the second power transfer stage when the first power storage device is electrically connected to the second power storage device.

* * * * *